(12) United States Patent
Snider et al.

(10) Patent No.: US 11,170,896 B2
(45) Date of Patent: *Nov. 9, 2021

(54) PREDICTING RISK OF MAJOR ADVERSE CARDIAC EVENTS

(71) Applicant: Critical Care Diagnostics, Inc., San Diego, CA (US)

(72) Inventors: James V. Snider, San Diego, CA (US); Eugene R. Heyman, Montgomery Village, MD (US)

(73) Assignee: Critical Care Diagnostics, Inc., San Diego, CA (US)

( * ) Notice: Subject to any disclaimer, the term of this patent is extended or adjusted under 35 U.S.C. 154(b) by 575 days.

This patent is subject to a terminal disclaimer.

(21) Appl. No.: 15/951,376

(22) Filed: Apr. 12, 2018

(65) Prior Publication Data

US 2018/0233229 A1     Aug. 16, 2018

Related U.S. Application Data

(63) Continuation of application No. 14/244,526, filed on Apr. 3, 2014, now Pat. No. 9,965,593, which is a
(Continued)

(51) Int. Cl.
*G16H 50/20* (2018.01)
*C12Q 1/6883* (2018.01)
(Continued)

(52) U.S. Cl.
CPC .......... *G16H 50/20* (2018.01); *C12Q 1/6883* (2013.01); *G01N 33/6869* (2013.01);
(Continued)

(58) Field of Classification Search
CPC ... A61P 9/00; A61P 9/04; A61P 21/00; G01N 2800/325; G01N 2800/50; G01N 2800/52;
(Continued)

(56) References Cited

U.S. PATENT DOCUMENTS 4,208,479 A   6/1980   Zuk et al.
5,206,140 A   4/1993   Marder et al.
(Continued)

FOREIGN PATENT DOCUMENTS

EP    1731910        12/2006
JP    H05-184384    7/1993
(Continued)

OTHER PUBLICATIONS

Januzzi et al. Arch Intern. Med. 166 (3): 315-320 (2006). from parent application.*

(Continued)

*Primary Examiner* — Mary K Zeman
(74) *Attorney, Agent, or Firm* — Fish & Richardson P.C.

(57) ABSTRACT

Measurement of circulating ST2 and natriuretic peptide (e.g., NT-proBNP) concentrations is useful for the prognostic evaluation of subjects, in particular for the prediction of adverse clinical outcomes, e.g., mortality, transplantation, and heart failure.

16 Claims, 13 Drawing Sheets

Related U.S. Application Data continuation of application No. 13/787,137, filed on Mar. 6, 2013, now Pat. No. 9,886,553, which is a continuation of application No. 13/299,612, filed on Nov. 18, 2011, now abandoned, which is a continuation of application No. 12/425,956, filed on Apr. 17, 2009, now Pat. No. 8,090,562.

(60) Provisional application No. 61/046,158, filed on Apr. 18, 2008.

(51) Int. Cl.
  *G01N 33/68* (2006.01)
  *G16H 50/30* (2018.01)
  *G01N 33/74* (2006.01)

(52) U.S. Cl.
  CPC ......... *G01N 33/6893* (2013.01); *G01N 33/74* (2013.01); *G16H 50/30* (2018.01); *C12Q 2600/158* (2013.01); *G01N 2333/58* (2013.01); *G01N 2333/7155* (2013.01); *G01N 2800/32* (2013.01); *G01N 2800/50* (2013.01)

(58) Field of Classification Search
  CPC .... G01N 2800/32; G01N 33/53; G01N 33/68; G01N 2333/475; G01N 2333/58; G01N 33/5091; G01N 2800/324; G01N 2800/326; G01N 33/57488; G01N 2800/60; G01N 33/6893; G01N 2333/47; G01N 2800/56; G01N 2333/7155; G01N 33/6869; G01N 2333/545; G01N 2015/1402; C12Q 2600/112; C12Q 2600/118; C12Q 1/6816; C12Q 2600/158; C12Q 2600/106; G16H 50/30; G16H 10/40; G16H 50/20; G16H 50/50; G16H 40/63; G16H 50/70; G06F 19/3431; G06F 19/345; G06F 19/22; G06F 19/3406; G06F 19/366; G06F 19/00; A61K 38/1793; A61K 38/18; A61K 38/191; A61K 2300/00; A61K 38/00; A61K 38/20; G06N 3/02; G06N 3/0454; G06N 3/0472; G06N 3/084; G06N 20/20; C12C 2600/118; C12C 1/6816; C12C 2600/158; G16B 40/00; G16B 40/30; G16B 30/20; G16B 20/00; G16B 30/00; G16B 25/10; G16B 25/00; G16B 30/10; G16B 35/10; G16B 40/20; G16B 50/30; G16B 5/00; C07K 16/244; C07K 14/7155; G06K 9/00563; G06K 9/6267; C40B 30/04; A61B 5/7275
  See application file for complete search history.

(56) References Cited

U.S. PATENT DOCUMENTS

| | | | |
|---|---|---|---|
| 5,217,899 A | 6/1993 | Shapiro et al. | |
| 5,348,879 A | 9/1994 | Shapiro et al. | |
| 5,786,163 A | 7/1998 | Hall | |
| 6,040,147 A | 3/2000 | Ridker et al. | |
| 6,210,976 B1 | 4/2001 | Sabbadini et al. | |
| 6,288,218 B1 | 9/2001 | Levinson | |
| 6,309,888 B1 | 10/2001 | Holvoet et al. | |
| 6,323,334 B1 | 11/2001 | Kingsbury et al. | |
| 6,677,124 B2 | 1/2004 | Tsuji et al. | |
| 6,810,284 B1 | 10/2004 | Bradley | |
| 6,905,827 B2 | 6/2005 | Wohlgemuth et al. | |
| 7,087,396 B2 | 8/2006 | Tominaga et al. | |
| 7,358,062 B2 | 4/2008 | Suovaniemi et al. | |
| 7,432,060 B2 | 10/2008 | Lee | |
| 7,655,415 B2* | 2/2010 | Lee | A61P 9/00 435/7.1 |
| 7,670,000 B2 | 3/2010 | Perie | |
| 7,670,769 B2 | 3/2010 | Lee | |
| 7,985,558 B2 | 7/2011 | Lee | |
| 7,989,210 B2 | 8/2011 | Lee | |
| 7,998,683 B2 | 8/2011 | Snider et al. | |
| 8,090,562 B2* | 1/2012 | Snider | G01N 33/74 703/11 |
| 8,147,817 B2 | 4/2012 | Lee et al. | |
| 8,420,785 B2 | 4/2013 | Snider et al. | |
| 8,530,173 B2 | 9/2013 | Lee | |
| 8,597,958 B2 | 12/2013 | Lee | |
| 8,617,825 B2* | 12/2013 | Snider | G06F 19/00 435/7.1 |
| 8,728,742 B2 | 1/2014 | Snider | |
| 8,734,769 B2 | 5/2014 | Lee | |
| 8,748,110 B2 | 6/2014 | Snider et al. | |
| 8,748,116 B2 | 6/2014 | Lee | |
| 8,871,452 B2 | 10/2014 | Lee | |
| 9,057,733 B2 | 6/2015 | Snider et al. | |
| 9,150,654 B2 | 10/2015 | Snider | |
| 9,239,333 B2 | 1/2016 | Snider | |
| D770,057 S | 10/2016 | Snider et al. | |
| 9,523,696 B2 | 12/2016 | Snider | |
| 9,551,708 B2* | 1/2017 | Snider | G01N 33/6869 |
| 9,568,481 B2 | 2/2017 | Snider | |
| 9,665,593 B2* | 5/2017 | Chen | G06F 16/178 |
| D800,332 S | 10/2017 | Snider et al. | |
| D800,333 S | 10/2017 | Snider et al. | |
| 9,823,257 B2 | 11/2017 | Snider | |
| 9,857,379 B2 | 1/2018 | Lee | |
| 9,886,533 B2* | 2/2018 | Boys | G06F 30/20 |
| 9,886,553 B2* | 2/2018 | Snider | C12Q 1/6883 |
| 9,934,249 B2 | 4/2018 | Tripathi et al. | |
| 9,965,593 B2* | 5/2018 | Snider | C12Q 1/6883 |
| 10,041,957 B2* | 8/2018 | Snider | A61P 25/00 |
| 10,067,146 B2* | 9/2018 | Snider | G01N 33/6869 |
| 10,203,339 B2* | 2/2019 | Snider | G01N 33/6869 |
| 10,303,844 B2* | 5/2019 | Snider | G16H 50/30 |
| 10,741,290 B2* | 8/2020 | Snider | G16H 50/30 |
| 10,745,484 B2* | 8/2020 | Snider | A61P 9/06 |
| 2002/0025559 A1 | 2/2002 | Tsuji et al. | |
| 2002/0072674 A1 | 6/2002 | Criton et al. | |
| 2002/0115081 A1 | 8/2002 | Lee et al. | |
| 2002/0172978 A1 | 11/2002 | Delmas et al. | |
| 2003/0109420 A1 | 6/2003 | Valkirs et al. | |
| 2003/0124624 A1* | 7/2003 | Tominaga | G01N 33/6893 435/7.9 |
| 2003/0228570 A1 | 12/2003 | Yat Wah Tom et al. | |
| 2004/0033993 A1 | 2/2004 | Sethi et al. | |
| 2004/0048286 A1* | 3/2004 | Lee | A61P 43/00 435/6.16 |
| 2004/0121343 A1 | 6/2004 | Buechler et al. | |
| 2004/0132013 A1 | 7/2004 | De Bold | |
| 2004/0133079 A1 | 7/2004 | Mazar et al. | |
| 2004/0220155 A1 | 11/2004 | Seibert | |
| 2004/0253637 A1 | 12/2004 | Buechler et al. | |
| 2005/0130136 A1 | 6/2005 | Lee et al. | |
| 2005/0196817 A1 | 9/2005 | Kingsmore et al. | |
| 2005/0203046 A1 | 9/2005 | Schmitz et al. | |
| 2005/0250156 A1 | 11/2005 | Shebuski et al. | |
| 2005/0272054 A1 | 12/2005 | Cargill et al. | |
| 2006/0216755 A1 | 9/2006 | Lee | |
| 2007/0021977 A1 | 1/2007 | Elsholz | |
| 2007/0042978 A1 | 2/2007 | Girard et al. | |
| 2007/0248981 A1 | 10/2007 | Snider et al. | |
| 2008/0003199 A1 | 1/2008 | Lee | |
| 2008/0233191 A1 | 9/2008 | Blackburn et al. | |
| 2009/0111708 A1 | 4/2009 | Seddon et al. | |
| 2009/0192078 A1 | 7/2009 | Lee | |
| 2009/0264779 A1 | 10/2009 | Snider et al. | |
| 2009/0305265 A1 | 12/2009 | Snider et al. | |
| 2010/0009356 A1 | 1/2010 | Snider et al. | |
| 2010/0055683 A1 | 3/2010 | Snider et al. | |
| 2010/0267062 A1 | 10/2010 | Frey et al. | |
| 2011/0008805 A1* | 1/2011 | Urdea | G01N 33/74 435/7.92 |
| 2011/0053170 A1 | 3/2011 | Snider et al. | |

(56) References Cited

U.S. PATENT DOCUMENTS

| | | |
|---|---|---|
| 2011/0127412 A1 | 6/2011 | Cheung |
| 2011/0137131 A1 | 6/2011 | Adourian et al. |
| 2011/0189698 A1* | 8/2011 | Burns ............... G01N 33/6893 435/7.4 |
| 2011/0250703 A1 | 10/2011 | Lee |
| 2011/0256635 A1 | 10/2011 | Snider |
| 2011/0262941 A1 | 10/2011 | Snider |
| 2011/0280887 A1 | 11/2011 | Lee |
| 2012/0040381 A1 | 2/2012 | Snider et al. |
| 2012/0065897 A1 | 3/2012 | Snider et al. |
| 2012/0276551 A1 | 11/2012 | Snider |
| 2013/0071404 A1 | 3/2013 | Snider et al. |
| 2013/0177931 A1 | 7/2013 | Snider et al. |
| 2013/0244236 A1 | 9/2013 | Snider et al. |
| 2013/0251664 A1 | 9/2013 | Lee |
| 2013/0273562 A1 | 10/2013 | Lee |
| 2013/0317030 A1 | 11/2013 | Lee |
| 2013/0345805 A1 | 12/2013 | Snider et al. |
| 2014/0045200 A1 | 2/2014 | Snider et al. |
| 2014/0051773 A1 | 2/2014 | Snider |
| 2014/0058743 A1 | 2/2014 | Snider et al. |
| 2014/0234875 A1 | 8/2014 | Snider |
| 2014/0286944 A1 | 9/2014 | Snider et al. |
| 2014/0302536 A1 | 10/2014 | Lee |
| 2015/0081224 A1 | 3/2015 | Snider et al. |
| 2015/0153360 A1 | 6/2015 | Lee |
| 2015/0177259 A1 | 6/2015 | Lee |
| 2015/0199491 A1 | 7/2015 | Snider et al. |
| 2015/0361177 A1 | 12/2015 | Snider |
| 2016/0169879 A1 | 6/2016 | Snider et al. |
| 2016/0169882 A1 | 6/2016 | Snider et al. |
| 2016/0299153 A1 | 10/2016 | Snider |
| 2018/0156818 A1 | 6/2018 | Lee |

FOREIGN PATENT DOCUMENTS

| | | |
|---|---|---|
| JP | 6178687 | 6/1994 |
| JP | 7031479 | 2/1995 |
| JP | 2005-291899 | 10/2005 |
| JP | 2.005-538700 | 12/2005 |
| JP | 2007-515632 | 6/2007 |
| JP | 2007-248395 | 9/2007 |
| JP | 2011-520098 | 7/2011 |
| JP | 2012-508386 | 4/2012 |
| RU | 2312591 | 12/2007 |
| RU | 2452394 | 6/2012 |
| WO | WO 1998/07754 | 2/1998 |
| WO | WO 1998/38311 | 9/1998 |
| WO | WO 1998/43090 | 10/1998 |
| WO | WO 1999/13331 | 3/1999 |
| WO | WO 1999/34217 | 7/1999 |
| WO | WO 00/35473 | 6/2000 |
| WO | WO 2000/35951 | 6/2000 |
| WO | WO 00/73498 | 12/2000 |
| WO | WO 01/021641 | 3/2001 |
| WO | WO 01/70817 | 9/2001 |
| WO | WO 01/73498 | 10/2001 |
| WO | WO 2002/38794 | 5/2002 |
| WO | WO 2003/094856 | 11/2003 |
| WO | WO 2003/100000 | 12/2003 |
| WO | WO 2004/056868 | 7/2004 |
| WO | WO 2005/041893 | 5/2005 |
| WO | WO 2005/055810 | 6/2005 |
| WO | WO 2005/079844 | 9/2005 |
| WO | WO 2006/077265 | 7/2006 |
| WO | WO 2007/127749 | 11/2007 |
| WO | WO 2007/130627 | 11/2007 |
| WO | WO 2007/130962 | 11/2007 |
| WO | WO 2007/131031 | 11/2007 |
| WO | WO 2007/143295 | 12/2007 |
| WO | WO 2009/007754 | 1/2009 |
| WO | WO 2009/129454 | 10/2009 |
| WO | WO 2011/127412 | 11/2011 |
| WO | WO 2012/059477 | 5/2012 |

OTHER PUBLICATIONS

Mueller et al. (Apr. 2008) Increased plasma concentrations of soluble ST2 are predictive for 1-year mortality in patients with acute destabilized heart failure. Clinical Chemistry vol. 54 No. 4 p. 752.*
Baggish et al. (Feb. 2008) amino-terminal Pro-B-Type Natriuretic peptide testing and prognosis in patients with acute dyspnea, including those with acute heart failure. American Journal of Cardiology, vol. 101, issue 3A, p. 49A.*
Balion et al. (2008, available online Oct. 2007) Physiological, pathological, pharmacological, biochemical and hematological factors affecting BNP and NT-proBNP. Clinical Biochemistry, vol. 41 p. 231.*
Bergler-Klein (2004) Natriuretic peptides predict symptom free survival and postoperative outcome in severe aortic stenosis. Circulation, vol. 109:2302-2308.*
Oremus, et al. (2008, available online Sep. 2007) A systematic review of BNP as a predictor of prognosis in persons with coronary artery disease. Clinical Biochemistry, 41: 260-265.*
Sabatine et al. (Mar. 31, 2008) Complementary roles for biomarkers of biomechanical strain ST2 and N-terminal prohormone P-type Natriuretic peptide in patients with ST-elevation myocardial infarction. Circulation, 117:1936-1944.*
Shimpo, et al. Serum levels of the interleukin-1 receptor family member ST2 predict mortality and clinical outcome in acute myocardial infarction. Circulation, 109:2186-2190.*
Levy, et al. (2006) The Seattle heart failure model. Circulation, 113:144-1433.*
U.S. Appl. No. 13/787,975, filed Mar. 7, 2013, Snider.
U.S. Appl. No. 13/969,116, filed Aug. 1, 2013, Snider.
U.S. Appl. No. 14/290,465, filed May 29, 2014, Lee.
U.S. Appl. No. 14/566,938, filed Dec. 11, 2014, Snider et al.
U.S. Appl. No. 14/566,955, filed Dec. 11, 2014, Snider et al.
U.S. Appl. No. 14/993,196, filed Jan. 12, 2016, Snider.
U.S. Appl. No. 15/370,049, filed Dec. 6, 2016, Snider et al.
U.S. Appl. No. 15/382,810, filed Dec. 19, 2016, Snider.
U.S. Appl. No. 15/385,095, filed Dec. 20, 2016, Snider et al.
U.S. Appl. No. 15/409,283, filed Jan. 18, 2017, Snider et al.
U.S. Appl. No. 15/410,155, filed Jan. 19, 2017, Snider et al.
[No Author Listed] "The Debate over Homeopathic Medicine," Yale Journal of Medicine and Law, 2011, vol. VII: 8 pages.
[No Author Listed] Monoclonal Antibody: Anti-Human ST2; Medical & Biological Laboratories Co., Ltd., Aug. 23, 2000, 2 pages.
[No Author Listed], web search results, "Information Hyperlinked Over Proteins—Symbol IL1RL1," 2006, 5 pages.
accessdata.fda.gov [online]. "Substantial Equivalence Determination Decision Summary Assay Only Template," Dec. 26, 2011 [retrieved on Nov. 28, 2017]. Retrieved from the Internet: URL <https://https://www.accessdata.fda.gov/cdrh_docs/reviews/k111452.pdf>, 17 pages.
Albert et al., "Prospective study of C-reactive protein, homocysteine, and plasma lipid levels as predictors of sudden cardiac death," Circulation, Jun. 4, 2002, 105(22):2595-9.
Allen et al., "Multi-marker strategies in heart failure: clinical and statistical approaches," Heart Failure Review, Jul. 2010, 15: 343-349.
Alleyne et al., "Cytochrome-c as Marker for MI 97 Cytochrome-c Detection A Diagnostic Marker for Myocardial Infarction," Applied Biochemistry and Biotechnology, Jan. 2001, 90: 97-105.
Anonymous: "Heart Failure Stages & Functional Classifications", Internet Citation, May 8, 2010 (May 8, 2010), pp. 1-4, XP002671183, Retrieved from the Internet: URL:http://web.archive.org/web/20100508015524/http://www.emoryhealthcare.org/heart-failure/learn-about-heart-failure/stages-classification/stages-classification.html.
Anwaruddin et al., "Renal function, congestive heart failure, and amino-terminal pro-brain natriuretic peptide measurement: results from the ProBNP Investigation of Dyspnea in the Emergency Department (PRIDE) Study," Journal of the American College of Cardiology, Jan. 3, 2006, 47(1): 91-97.
AU Office Action in Australian Appln. No. 2007244927, dated Nov. 22, 2010, 10 pages.

(56) References Cited

OTHER PUBLICATIONS

AU Office Action in Australian Appln. No. 2007248160, dated Jan. 29, 2010, 3 pages.
AU Office Action in Australian Appln. No. 2009236109, dated May 12, 2014, 3 pages.
AU Office Action in Australian Appln. No. 2011203031, dated Aug. 17, 2012, 2 pages.
AU Office Action in Australian Appln. No. 2012202069, dated Jan. 17, 2014, 4 pages.
AU Office Action in Australian Appln. No. 2012202069, dated Jul. 10, 2015, 13 pages.
AU Office Action in Australian Appln. No. 2013204539, dated Jan. 17, 2014, 4 pages.
AU Office Action in Australian Appln. No. 2013204539, dated Jul. 10, 2015, 4 pages.
AU Office Action in Australian Appln. No. 2013305829, dated Jan. 31, 2019, 4 pages.
AU Office Action in Australian Appln. No. 2013305829, dated Mar. 21, 2018, 3 pages.
AU Office Action in Australian Appln. No. 2016200419, dated Jan. 12, 2017, 7 pages.
AU Office Action in Australian Appln. No. 2016201172, dated Mar. 28, 2017, 8 pages.
AU Office Action in Australian Appln. No. 2019201709, dated Apr. 8, 2020, 9 pages.
Auer et al., "C-reactive protein and coronary artery disease." Japan Heart Journal, Mar. 6, 2002, 43(6):607-619.
Aukrust et al., "Cytokine network in congestive heart failure secondary to ischemic or idiopathic dilated cardiomyopathy," American Journal of Cardiology, Feb. 1, 1999, 83(3):376-382.
Backkevold et al., "Molecular characterization of NF-HEV, a nuclear factor preferentially expressed in human high endothelial venules," American Journal of Pathology, Jul. 2003, 163(1):69-79.
Baggish et al., "A validated clinical and biochemical score for the diagnosis of acute heart failure: The ProBNP Investigation of Dyspnea in the Emergency Department (PRIDE) Acute Heart Failure Score," American Heart Journal, Jan. 2006. 151:48-54
Baumgarten et al., "Cytokines as emerging targets in the treatment of heart failure," Trends Cardiovasc Medicine, Jul. 2000, 10(5):216-223.
Bayés-Genis, Antoni, "The circulating NTproBNP level, a new biomarker for the diagnosis of heart failure in patients with acute shortness of breath," Revista Española de Cardiologia, Oct. 2005, 58(10): 1142-1144.
Belch et al., "Oxygen free radicals and congestive heart failure," Heart, Jan. 17, 1999, 65(5):245-48.
Blum et al., "Pathophysiological role of cytokines in congestive heart failure," Annual Review of Medicine, Feb. 2001, 52:15-27.
Boisot et al., "Serial Sampling of ST2 Predicts 90-Day Mortality Following Destabilized Heart Failure," Journal of Cardiac Failure. Nov. 1, 2008, 14:732-738.
Brint et al., "ST2 is an inhibitor of interleukin 1 receptor and Toll-like receptor 4 signaling and maintains endotoxin tolerance," Nature Immunology. Apr. 2004, 5(4):373-9.
Brown, "Techniques for Mechanical Stimulation of cells in vitro: a review," Journal of Biomechanics, Jan. 2000, 33:3-14.
Bruneau et al., "Selective changes in natriuretic peptide and early response gene expression in isolated rat atria following stimulation by stretch or endothelin-1," Cardiovascular Research, Oct. 1994, 28(10): 1519-1525.
Brunner et al., "Increased levels of soluble ST2 protein and IgG1 production in patients with sepsis and trauma. Intensive care medicine," Jul. 1, 2004, 30(7):1468-73.
CA Examiner's Report: Canadian Patent Application No. 2,650,201; dated Aug. 19, 2010.
CA Office Action in Canadian Appln. No. 2,484,897, dated Dec. 20, 2010, 5 pages.
CA Office Action in Canadian Appln. No. 2,484,897, dated Feb. 24, 2012, 3 pages.
CA Office Action in Canadian Appln. No. 2,484,897, dated Feb. 4, 2014, 2 pages.
CA Office Action in Canadian Appln. No. 2,484,897, dated Mar. 21, 2013, 2 pages.
CA Office Action in Canadian Appln. No. 2,640,201, dated Aug. 19, 2010, 4 pages.
CA Office Action in Canadian Appln. No. 2,650,201, dated Apr. 26, 2018, 6 pages.
CA Office Action in Canadian Appln. No. 2,650,201, dated Aug. 19, 2010, 4 pages.
CA Office Action in Canadian Appln. No. 2,650,201, dated Dec. 15, 2011, 3 pages.
CA Office Action in Canadian Appln. No. 2,650,201, dated Feb. 5, 2020, 4 pages.
CA Office Action in Canadian Appln. No. 2,650,201, dated Jul. 28, 2015, 22 pages.
CA Office Action in Canadian Appln. No. 2,650,201, dated Jun. 19, 2019, 12 pages.
CA Office Action in Canadian Appln. No. 2,650,201, dated Jun. 5, 2017, 4 pages.
CA Office Action in Canadian Appln. No. 2,650,963, dated Aug. 17, 2015, 5 pages.
CA Office Action in Canadian Appln. No. 2,650,963, dated Aug. 18, 2010, 5 pages.
CA Office Action in Canadian Appln. No. 2,650,963, dated Jun. 25, 2019, 4 pages.
CA Office Action in Canadian Appln. No. 2,650,963, dated Mar. 31, 2016, 13 pages.
CA Office Action in Canadian Appln. No. 2,650,963, dated Nov. 1, 2017, 18 pages.
CA Office Action in Canadian Appln. No. 2,630,96b, dated Oct. 26, 2011, 5 pages.
CA Office Action in Canadian Appln. No. 2,720,674, dated Jan. 19, 2016, 15 pages.
CA Office Action in Canadian Appln. No. 2,720,674, dated Oct. 30, 2017, 9 pages.
CA Office Action in Canadian Appln. No. 2,882,303, dated Apr. 24, 2019, 4 pages.
Cabell et al., "Importance of echocardiography in patients with severe nonischemic heart failure: the second Prospective Randomized Amlodipine Survival Evaluation (PRAISE-2) echocardiographic study," American Heart Journal, Jan. 1, 2004, 147(1):151-7.
Carter et al., "Regulation of ST2L expression on T helper (Th) type 2 cells," European Journal of Immunology, Oct. 2001, 31(10):2979-85.
Chan et al., "Human IL018 Receptor and ST2L are Stable and Selective Markers for the Respective Type I and Type 2 Circulating Lymphocytes," The Journal of Immunology, Aug. 1, 2001, 167(3) 1238-1244.
Cheng et al., "Mechanical strain tightly controls fibroblast growth factor-2 release from cultured human vascular smooth muscle cells," Circulation Research, Jan. 1, 1997, 80(1):28-36 (abstract).
Clerico et al., "Diagnostic accuracy and prognostic relevance of the measurement of cardiac natriuretic peptides: a review," Clinical Chemistry, Jan. 1, 2004, 50(1):33-50.
CN Fourth Office Action; Chinese Patent Application No. 03 816298.9; dated 2011.
CN Notification of Reexamination in CN Appln. No. 201380004793.8, dated Oct. 22, 2019, 9 pages (with English translation).
CN Office Action in Chinese Appln. No. 03816298.9, dated Aug. 12, 2011, 3 pages (English translation only).
CN Office Action in Chinese Appln. No. 03816298.9, dated Dec. 25, 2007, 3 pages (with English translation).
CN Office Action in Chinese Appln. No. 03816298.9, dated Sep. 8, 2006, 4 pages (with English translation).
CN Office Action in Chinese Appln. No. 201110387886.6, dated Apr. 27, 2013, 12 pages (with English translation).
CN Office Action in Chinese Appln. No. 201110387886.6, dated Dec. 19, 2013, 9 pages (with English translation).
CN Office Action in Chinese Appln. No. 201380054795.8, dated Apr. 24, 2019, 10 pages (English translation).
CN Office Action in Chinese Appln. No. 201380054795.8, dated July 6, 2017, 9 pages (with English translation).

(56) References Cited

OTHER PUBLICATIONS

CN Office Action in Chinese Appln. No. 201380054795.8, dated Mar. 6, 2018, 8 pages (English translation).
CN Office Action in Chinese Appln. No. 201380054795.8, dated Oct. 22, 2018, 11 pages (English translation).
CN Office Action in Chinese Appln. No. CN 03816298.9, dated Nov. 6, 2009, 5 pages (with English Translation).
Conklin, "B-type natriuretic peptide: a new measurement to distinguish cardiac from pulmonary' causes of acute dyspnea," Journal of Emergency Nursing, Jan. 1, 2005, (31):73-5.
Coyle et al., "Crucial role of the interleukin 1 receptor family member T1/ST2 in T helper cell type 2-mediated lung mucosal immune responses," Journal of Experimental Medicine, Oct. 4, 1999. 190(7): 895-902.
Dale et al., "Interleukin-1 Receptor Cluster: Gene Organization ofIL1R2, IL1R1, IL1RL2 (IL-1Rrp2), IL1RL1 (T1/ST2), andIL18R1 (IL-1Rrp) on Human Chromosome 2q.," Genomics, Apr. 1, 1999, 57(1):177-9.
De Keulenaer et al., "Identification of IEX-1 as a biomechanically controlled nuclear factor-κB target gene that inhibits cardiomyocyte hypertrophy," Circulation Research, Apr. 5, 2002, 90(6):690-6.
Dhalla et al., "Measurement of adrenolutin as an oxidation product of catecholamines in plasma," Molecular and Cellular Biochemistry', May 1, 1989, 87(1):85-92.
Di Serio et al., "Integration between point-of-care cardiac markers in an emergency/cardiology department and the central laboratory: methodological and preliminary clinical evaluation," Clinical Chemistry and Laboratory Medicine (CCLM), Apr. 1, 2005, 43(2):202-9.
ELECSYS® ProBNP assay, Roche Diagnostics, Indianapolis, IN, package insert v.7, Jul. 2007, 1 page.
En.wikipedia.org [online]. "ST2 cardiac biomarker," dated Jul. 14, 2012 [retrieved on Feb. 29, 2016]. Retrieved from the Internet: <https://en.wikipedia.org/w/index.php?title=ST2_cardiac_biomarker&oldid=502 1 98259>. 3 pages.
EP Communication in European Appln. No. 03728848.7, dated Jun. 7, 2010, 7 pages.
EP Communication in European Appln. No. 09731842.2, dated Nov. 13, 2012, 3 pages.
EP Communication in European Appln. No. 10184644.2, dated Apr. 28, 2014, 2 pages.
EP Conununication in European Appln. No. 10184644.2, dated Dec. 10, 2012, 5 pages.
EP Communication in European Appln. No. 10184644.2, dated Feb. 2, 2012, 6 pages.
EP Communication in European Appln. No. 11177461.8, dated Sep. 22, 2011, 2 pages.
EP Communication in European Appln. No. 12152464.9, dated, Dec. 18, 2013, 2 pages.
EP Communication in European Appln. No. 14188319.9, dated Feb. 13, 2015, 1 page.
EP Communication in European Appln. No. 14188319.9, dated Jan. 4, 2016, 2 pages.
EP Communication; European Patent Application No. 03728848.7; dated Nov. 30. 2009.
EP European Office Action in European Appln. No. 14188319, dated Jan. 4, 2016, 5 pages.
EP European Office Action in European Appln. No. 15163587.7, dated May 22, 2017, 4 pages.
EP European Office Action in European Appln. No. 15198075.2, dated Jun. 1, 2017, 6 pages.
EP European Office Action in European Appln. No. 16158762.1, dated May 17, 2017, 6 pages.
EP European Search Report in European Appln. No. 07761666.2, dated Sep. 30, 2009, 20 pages.
EP European Search Report in European Appln. No. 07761742.1, dated Nov. 12, 2009, 13 pages.
EP European Search Report in European Appln. No. 10171764.3, dated Sep. 24, 2010, 3 pages.
EP European Search Report in European Appln. No. 10171764.3, dated Oct. 6, 2010, 6 pages.
EP European Search Report in European Appln. No. 10184644.2, dated May 2, 2011, 6 pages.
EP European Search Report in European Appln. No. 11177461.8, dated Aug. 2, 2013, 7 pages.
EP European Search Report in European Appln. No. 11177461.8, dated Jan. 23, 2012, 14 pages.
EP European Search Report in European Appln. No. 12152464.9, dated Jul. 4, 2012, 3 pages.
EP European Search Report in European Appln. No. 13179055, dated Sep. 25, 2013, 3 pages.
EP European Search Report in European Appln. No. 13179055.2, dated Sep. 13, 2013, 4 pages.
EP European Search Report in European Appln. No. 14188319.9, dated Feb. 13, 2015, 6 pages.
EP European Search Report in European Appln. No. 15163587.7, dated Feb. 11, 2016, 7 pages.
EP European Search Report in European Appln. No. 15198075.2, dated Jul. 20, 2016, 11 pages.
EP European Search Report in European Appln. No. 16158762, dated Jun. 10, 2016, 9 pages.
EP European Search Report in European Appln. No. 2010912, dated Apr. 9, 2009, 9 pages.
EP European Search Report; European Patent Application No. 11177461.8-1223; dated Jan. 23, 2012.
EP Extended European Search Report in European Appln. No. 14177846.4, dated Jan. 5, 2015, 5 pages.
EP Extended European Search Report in European Appln. No. 16166093.1, dated Sep. 12, 2016, 7 pages.
EP Extended European Search Report in European Appln. No. 17177530.7, dated Aug. 28, 2017, 11 pages.
EP Extended European Search Report in European Appln, No. 18166387.3, dated Jun. 15, 2018, 5 pages.
EP Extended European Search Report in European Appln. No. 18182529.0, dated Sep. 21, 2018, 9 pages.
EP Office Action in European Application No. 13831501.5, dated May 15, 2020, 7 pages.
EP Office Action in European Appln. No. 07761742.1, dated Apr. 2, 2013, 5 pages.
EP Office Action in European Appln. No. 07761742.1, dated Jan. 25, 2011, 6 pages.
EP Office Action in European Appln. No. 0/761742.1, dated Mar. 12, 2012, 8 pages.
EP Office Action in European Appln. No. 13831501.5, dated May 23, 2018, 11 pages.
EP Office Action in European Appln. No. 15163587.7, dated Feb. 14, 2018, 4 pages.
EP Office Action in European Appln. No. 15198075.2, dated Jan. 17, 2018, 5 pages.
EP Office Action in European Appln. No. 18182529, dated Mar. 19, 2020, 6 pages.
EP Partial European Search Report in European Appln. No. 11177461, dated Sep. 22, 2011, 6 pages.
EP Summons to Attend Oral Proceedings in European Appln. No. 07811859.3, dated Sep. 27, 2010, 3 pages.
EP Supplementary European Search Report in European Appln. No. 03728848.7, dated Dec. 15, 2005, 2 pages.
EP Supplementary European Search Report in European Appln. No. 13831501.5, dated Mar. 14, 2016, 1 page.
EP Supplementary European Search Report in European Appln. No. EP 09731842.2, Apr. 1, 2011, 2 pages.
EP Supplementary Search Report in European Appln. No. 07811859, dated Jul. 6, 2009, 9 pages.
EP Supplementary Search Report in European Appln. No. 07761219.0, dated May 13, 2009, 9 pages.
FDA, Substantial Equivalence Determination Decision Summary, Dec. 26, 2011, Food And Drag Administration, http://www.accessdata.fda.gov/cdrh docs/reviews/K111452.pdf, 2011, 17 pages.
Feldman et al., "C-reactive protein is an independent predictor of mortality in women with HIV-1 infection," JAIDS Journal of Acquired Immune Deficiency Syndromes, Feb. 1, 2003. 32(2):210-4.

(56) References Cited

OTHER PUBLICATIONS

Feng et al., "Transcriptional profile of mechanically induced genes in human vascular smooth muscle cells," Circulation Research, Dec. 3, 1999 Dec. 3, 85(12): 1118-23.
Figal et al., "Usefulness of NTproBNP in the emergency management of patients with severe dyspnea and an uncertain heart failure diagnosis," Revista Española de Cardiologia (English Edition), Oct. 1, 2005, 58(10):1155-61.
Fonarow et al., "The confounding issue of comorbid renal insufficiency," The American Journal of Medicine, Dec. 1, 2006, 119(12):S17-25.
Forssmann et al. "The heart is the center of a new endocrine, paracrine, and neuroendocrine system," Archives of History and Cytology, Dec. 31, 1988, 52:293-315.
Frangogiannis et al., "Resident cardiac mast cells degranulate and release preformed TNE-alpha, initiating the cytokine cascade in experimental canine myocardial ischemia/reperfusion," Circulation, Aug. 18, 1988, 98(7):699-710.
Galvani et al., "Prognostic influence of elevated values of cardiac troponin I in patients with unstable angina," Circulation, Apr. 15, 1997, 95(8):2053-2059.
Gegenhuber et al., "B-type natriuretic peptide and amino terminal proBNP predict one-year mortality in short of breath patients independently of the baseline diagnosis of acute destabilized heart failure," Clinica Chimica Acta, August 1. 2006, 370(1-2): 174-179.
GenBank Accession No. AAA67172, "Fit-1S [Rattus norvegicus]," May 23, 1995, 2 pages.
GenBank Accession No. AB012701, "Homo sapiens mRNA for ST2L, 5' noncoding region including distal exon (exon 1a), complete cds," Aug. 24, 2000, 2 pages.
GenBank Accession No. AB022176, "Homo sapiens ST2 gene for interleukin-1 receptor-related protein, exon 1a," Sep. 15, 2007, 2 pages.
GenBank Accession No. AB024518, "Homo sapiens mRNA for DVS27-related protein, complete cds," Mar. 10, 1999, 2 pages.
GenBank Accession No. AB029084, "Homo sapiens ST2V mRNA, complete cds," Oct. 31, 1999, 2 pages.
GenBank Accession No. AC007248, "Homo sapiens BAG clone RPI1-315022 from 2," Apr. 21, 2005, 55 pages.
GenBank Accession No. AL117622, "Homo sapiens mRNA; cDNA DKFZp564N 1164 (from clone DKFZp564Nl 164)," Feb. 18, 2000, 2 pages.
GenBank Accession No. D12763, "Homo sapiens mRNA for ST2 protein," Jan. 23, 2003, 2 pages.
GenBank Accession No. D12764, "Homo sapiens DNA for ST2, partial cds," May 29, 2002, 2 pages.
GenBank Accession No. E07714, "cDNA encoding mouse ST2 protein," Nov. 4, 2005, 2 pages.
GenBank Accession No. E07716, "cDNA encoding human ST2," Sep. 27, 1997, 2 pages.
GenBank Accession No. E08652, "cDNA encoding mouse ST2L which is produced specifically when cell is moving stage G0 to stage G1" Sep. 29, 1997, 1 page.
GenBank Accession No. NM_003856.2, "Homo sapiens interleukin 1 receptor like 1 (ILIRL1), transcript variant 2, mRNA," Jan. 24, 2003. 4 page GenBank Accession No. NM 013037, "Rattus norvegicus interleukin 1 receptor-like 1 (IIIr 1), transcript variant 1, mRNA," Nov. 17, 2006, 3 pages.
GenBank Accession No. NM_013037, "Rattus norvegicus interleukin 1 receptor-like 1 (I11rl1), transcript variant 1, mRNA," Nov. 17, 2006, 3 pages.
GenBank Accession No. NM_016232.4, "Homo sapiens interleukin 1 receptor-like 1 (IL1RL1), transcript variant 1, mRNA," Jan. 24, 2003, 4 pages.
GenBank Accession No. NM_033439.2, "Homo sapiens interleukin 33 (IL33), mRNA," Feb. 15, 2009, 6 pages.
GenBank Accession No. NP_003847.2, "interleukin-1 receptor-like 1 isoform 2 precursor [Homo sapiens]," Jan. 24, 2003, 4 pages.
GenBank Accession No. NP_057316.3, "interleukin-1 receptor-like 1 isoform 1 precursor [Homo sapiens]," Jan. 24, 2003, 4 pages.
GenBank Accession No. NP_254274.1, "interleukin-33 isoform a precursor [Homo sapiens]," Jul. 13, 2008, 1 page.
GenBank Accession No. U04317, "Rattus norvegicus Fit-1M (Fit-1) mRNA, complete cds," May 27, 1994, 2 pages.
GenBank Accession No. U04319, "Rattus norvegicus Fit-1S (Fit-1) mRNA, complete cds," May 24, 1995, 2 pages.
GenBank Accession No. X60184, "Mouse ST2 gene for growth-associated protein," Nov. 14, 2006, 5 pages.
GenBank Accession No. Y07519, "Mouse ST2 gene," Mar. 23, 1995, 3 pages.
GeneID: 90865, IL33, "interleukin 33 [Homo sapiens],"Jul. 22, 2008, 1 page.
GeneID: 9173, IL1RL1, "interleukin 1 receptor-like 1 [ Homo sapiens]," updated Jul. 22, 2008, 1 page.
Gillespie et al., "Unexplained dyspnea," Mayo Clinic Proceeding, Jul. 1, 1994, 69(7):657-63.
Goetze et al., "B-type natriuretic peptide and its precursor in cardiac venous blood from failing hearts," European Journal of Heart, Failure, Jan. 7, 2005, (1):69-74.
Goldstein, "Plasma norepinephrine as an indicator of sympathetic neural activity in clinical cardiology," American Journal of Cardiology, Dec. 1, 1981, 48(6): 1147-54.
Green et al. "Use of Troponin T and Creatine Kinase-MB Subunit Levels for Risk Stratification of Emergency Department Patients With Possible Myocardial Ischemia." Annals of Emergency Medicine, Jan. 1998, 31(1):19-29.
Gutstein et al., "Role of inositol 1, 4, 5-trisphosphate receptors in regulating apoptotic signaling and heart failure," Heart and Vessels, Dec. 31, 1996, 53-7.
Gwechenberger et al., "Cardiac myocytes produce interleukin-6 in culture and in viable border zone of reperfused infarctions," Circulation, Feb. 2, 1999, 99(4):546-51.
Hall et al., "N-terminal proatrial natriuretic factor. An independent predictor of long-term prognosis after myocardial infarction," Circulation, May 1994, 89(5): 1934-42.
Hanyu et al., "Urinary thrombomodulin in patients with rheumatoid arthritis: relationship to disease subset," Clinical Rheumatology, Sep. 1, 1999, 18(5):385-9.
Hasdai et al., "Increased serum concentrations of interleukin-1 beta in patients with coronary arterv disease." Heart, Jul. 1996, 76:(1): 24-28'.
Heeschen et al.. "Predictive value of C-reactive protein and troponin T inpatients with unstable angina: a comparative analvsis. CAPTURE Investigators, Chimeric c7E3 AntiPlatelet Therapv in Unstable angina Refractor to standard treatment trial," Journal of the American College of Cardiology, May 1, 2000, 35(6): 1535-42.
Hirota et al., "Loss of a gp130 cardiac muscle cell survival pathway is a critical event in the onset of heart failure during biomechanical stress," Cell, Apr. 16, 1999, 97(2): 189-98.
IN Office Action in Indian Appin. No. 1767/DELNP/2015, dated Aug. 19, 2020, 5 pages.
Iwahana et al., "Different promoter usage and multiple transcription initiation sites of the interleukin-1 receptor-related human ST2 gene in UT-7 and TM12 cells," European Journal of Biochemistry, Sep. 1, 1999, 264(2):397-406.
Izakov et al., "Cooperative effects due to calcium binding by troponin and their consequences for contraction and relaxation of cardiac muscle under various conditions of mechanical loading," Circulation Research, Nov. 1991, 69(5): 1171-84.
Januzzi et al.. "NT-proBNP testing for diagnosis and short-term prognosis in acute destabilized heart failure: an international pooled analysis of 1256 patients: the International Collaborative of NT-proBNP Study," European Heart Journal, Feb. 1, 2006, 27(3):330-7.
Januzzi et al., "The N-terminal Pro-BNP investigation of dyspnea in the emergency department (PRIDE) study," The American Journal of Cardiology, Apr. 15, 2005, 95(8):948-54.
Januzzi et al., "Measurement of the Interleukin Family Member ST2 in Patients with Acute Dyspnea: Results from the PRIDE (Pro-Brain Natriuretic Peptide Investigation of Dyspnea in the Emergency Department) Study," Journal of the American College of Cardiology, Aug. 14, 2007, 50:607-613.

(56) References Cited

OTHER PUBLICATIONS

Januzzi et al., "Natriuretic peptide testing for the evaluation of critically ill patients with shock m the intensive care unit: a prospective cohort study," Critical Care, Feb. 2006, 10(1):R37, 7 pages.

Januzzi et al., "The value of soluble ST2 measurement for the diagnostic and prognostic evaluation of patients with acute dyspnea," Circulation, Oct. 31, 2006, 114(18):721.

Januzzi et al., "Utility of amino-terminal pro-brain natriuretic Peptide testing for prediction of 1-year mortality in patients with dyspnea treated in the emergency department," Archives of Internal Medicine, Feb. 13, 2006, 166(3):315-20.

Joyce et al., "Two inhibitors of pro-inflammatory cytokine release, interleukin-10 and interleukin-4, have contrasting effects on release of soluble p75 tumor necrosis factor receptor by cultured monocytes," European Journal of Immunology, Nov. 1994, 24(11):2699-705.

JP Decision to Grant a Patent in Japanese Appin. No. 2018-230514, dated Oct. 17, 2019, 5 pages (with English translation).

JP Japanese Office Action in Appln. No. 2015-528625, dated Jun. 5, 2017, 10 pages (with English translation).

JP Notice of Reasons for Rejection for Japanese Patent Application No. 2014-082442, dated Mar. 2, 2015, 4 pages (with English translation).

JP Notice of Reasons for Rejection in Japanese Appln. No. 2012-100940, dated Jan. 8, 2014, 6 pages (with English translation).

JP Notice of Reasons for Rejection in Japanese Appln. No. JP 2009-507931, dated Aug. 20, 2012, 2 pages (with English translation).

JP Notice of Reasons for Rejection in Japanese Appln. No. JP 2009-507931, dated Oct. 26, 2011, 3 pages (with English translation).

JP Notice of Reasons for Rejection in Japanese Appln. No. JP 2012-100940, dated Jan. 8, 2014, 15 pages (with English translation).

JP Office Action in Japanese Appl. No. 2009-510021, dated Oct. 22, 2012, 2 pages (English translation).

JP Office Action in Japanese Appln. No. 2009-173539, dated Sep. 20, 2011, 4 pages (with English translation).

JP Office Action in Japanese Appln No. 2011-505224, dated Sep. 4, 2013, 6 pages (with English translation).

JP Office Action in Japanese Appln. No. 2015-173815, dated Aug. 3, 2016, 6 pages (with English translation).

JP Office Action in Japanese Appln. No. 2016-006007, dated Dec. 8, 2016, 45pages (with English translation).

JP Office Action in Japanese Appln. No. 2017-162932, dated Jun. 27, 2018, 8 pages (with English Translation).

JP Office Action in Japanese Appln. No. 2017-178945, dated Jul. 5, 2018, 8 pages (with English Translation).

JP Office Action in Japanese Appln. No. 2019-026401, dated Apr. 13, 2020, 6 pages (with English translation).

JP Office Action in Japanese Appln. No. 2019-026401, dated Dec. 23, 2019, 8 pages (with English translation).

JP Office Action in Japanese Appln. No. 2019-208375, dated Sep. 9, 2020, 6 pages (with English translation).

JP Office Action in Japanese Patent Appl. No. 2015-528625, dated Mar. 26, 2018, 2 pages (English translation).

JP Office Action in Japanese Patent Appln. No. 2012-100940, dated Dec. 3, 2014, 9 pages (with English translation).

JP Office Action in Japanese Patent Appln. No. 2014-261824, dated Nov. 30, 2015, 6 pages (with English translation).

Kakkar et al., "The IL-33/ST2 pathway: Therapeutic target and novel biomarker," Nature Reviews Drug Discovery , 7(10):827-840 (2008).

KIDA et al., Pathophysiological role of natriuretic peptides. Rinsho Byori. Aug. 1989;37(8):875-82. Abstract Only.

Kieser et al., "Identification of the primary growth response gene, ST2/TI , as a gene whose expression is differentially regulated by different protein kinase C isozymes," FEBS Lett., 372(2-3): 189-193 (1995).

Kip et al.; "The problem with composite end points in cardiovascular studies," J. Am. Coll. Cardiol. 51:701-707 (2008).

Knudsen et al., "Predictors of elevated B-type natriuretic peptide concentrations in dyspneic patients without heart failure: an analysis from the breathing not properly multinational study," Ann. Emerg. Med., 45(6):573-580 (2005).

Krauser et al., "Effect of body mass index on natriuretic peptide levels in patients with acute congestive heart failure: a ProBNP Investigation of Dyspnea in the Emergency Department (PRIDE) substudy," Am. Heart J., 149(4):744-750 (2005).

Kumar et al., "ST2/T1 protein functionally binds to two secreted proteins from Balb/c 3T3 and human umbilical vein endothelial cells but does not bind interleukin 1," Journal of Biological Chemistry, Nov. 17, 1995. 270(46):27905-13.

Kumar et al., Expression of ST2, an interleukin-1 receptor homologue, is induced by proinflammatory stimuli. Biochem Biophys Res Commun. Jun. 27, 1997;235(3):474-8.

Kurioiwa et al., "Identification of Human ST2 Protein in the Sera of Patients with Autoimmune Diseases," Biochemical and Biophysical Research Communications 284:1104-8 (2001).

Kuroiwa et al., "Construction of ELISA system to quantify human ST2 protein in sera of patients. Hybridoma," 19(2): 151-159 (2000).

Laine et al., "Effect of ryanodine on atrial natriuretic peptide secretion bv contracting and quiescent rat atrium," Pflugers Archiv, Feb. 1, 1994, 426(3-4):276-83.

Lammerding et al., "Mechanotransduction in cardiac myocytes," Annals of the New York Academy of Sciences, May 2004, 1015(1):53-70.

Lee et al., "Novel markers for heart failure diagnosis and prognosis," Curr Opin Cardiol, 20(3):201-210 (2005).

Leyva et al., "Uric acid in chronic heart failure: a marker of chronic inflammation," European Heart J., 1998, 19:1814-1822.

Linares et al., "C-reactive protein (CRP) levels in systemic lupus erythematosus (SLE)," Clinical Rheumatology, Mar. 1, 1986, 5(1):66-9.

Lohning et al., "T1/ST2 is preferentially expressed on murine Th2 cells, independent of interleukin 4, interleukin 5, and interleukin 10, and important for Th2 effector function," Proc. Natl. Acad. Sci. U.S.A., 95(12):6930-6935 (1998).

Long, "The role of interleukin-1 in the failing heart," Heart Failure Reviews. Mar. 2001. 6:(2):81-94.

MacGowan et al., "Circulating interleukin-6 in severe heart failure," Am J Cardiol., 79(8): 1128-31 (1997).

MacKenna et al., Role of mechanical factors in modulating cardiac fibroblast function and extracellular matrix svnthesis. Cardiovasc. Res., 46(2):257-63 (2000).

Maisel et al., "Bedside B-Type Natriuretic Peptide in the Emergency Diagnosis of Heart Failure With Reduced or Preserved Ejection Fraction," J. Am. Coll. Cardiol., 2003, 41:2010-7i.

Maisel et al., "Primary results of the Rapid Emergency Department Heart Failure Outpatient Trial (Redhot). A multicenter study of B-type natriuretic peptide levels, emergency department decision making, and outcomes in patients presenting with shortness of breath," J. Am. Coll. Cardiol, 2004, 44(6): 1328-1333.

Maisel et al., "Rapid measurement of B-type natriuretic peptide in the emergency diagnosis of heart failure," N. Engl. J. Med, 347(3): 161-167 (2002).

Mann et al., "Stress activated cytokines and the heart," Cytokine Growth Factor Rev. 7(4):341-54 (1996).

Maxwell et al., "Influence of progressive renal dysfunction in chronic heart failure," European Journal of Heart Failure, Mar. 2002, 4(2): 125-30.

Mayo Clinic, Interpretive Handbook Test 61723: 5T2. Serum, Aug. 8, 2012, Mayo Medical Laboratories, http://www.nnayonnedicallaboratories.conn/interpretive-guide/?alpha=S&unitcode=61723, pp. 1-3 (Year: 2012).

Mayo et al., "Brain natriuretic peptide (BNP) testing in the emergency department," The Journal of Emergency Medicine, Aug. 1, 2006, 31(2):201-10.

McCord et al., "Relationship between obesity and B-type natriuretic peptide levels," Arch. Intern. Med, 164(20):2247-2252 (2004).

McCullough el al, "B-type natriuretic peptide and renal function in the diagnosis of heart failure: an analysis from the Breathing Not

(56) References Cited

OTHER PUBLICATIONS

Properly Multinational Study," American Journal of Kidney Diseases, Mar. 1, 2003, 41(3):571-9.
Mehra et al., "Obesity and suppressed B-type natriuretic peptide levels in heart failure," Journal of the American College of Cardiology, May 5, 2004, 43(9): 1590-5.
Millenium Pharmaceuticals, Inc. Millenium Pharmaceuticals Identifies a Key mediator of Allergic Immune Response. Press Release Oct. 4, 1999, 2 pages.
Mitcham et al., "T1/ST2 signaling establishes it as a member of an expanding interleukin-1 receptor family," J Biol. Chem. Mar. 1996, 8,271(10):5777-83.
Moe et al., "Neurohormonal activation in severe heart failure: relations to patient death and the effect of treatment with flosequinan," American Heart Journal, Apr. 1, 2000, 139(4):587-95.
Morgan el al, "Diagnostic Evaluation of Dyspnea," American Family Physician, Feb. 1998, 57(4):711-716.
Morrison et al., "Utility of a Rapid B-Natriuretio Peptide Assay in Differentiating Congestive Heart Failure from Lung Disease in Patients Presenting With Dyspnea," Journal of American College of Cardiology, 39: 202-209 (2002).
Mueller et al., "Use of B-type natriuretic peptide for the management of women with dyspnea," The American Journal of Cardiology, Dec. 15, 2004, 94(12):1510-4.
Mueller et al., "Increased Plasma Concentrations of Soluble ST2 are Predictive for 1-Year Mortality in Patients with Acute Destabilized Heart Failure," Clinical Chemistry, Apr. 1, 2008, 54:752-756.
Mueller el al, "Use of B-type natriuretic peptide in the evaluation and management of acute dyspnea," New England Journal of Medicine, 350(7):647-654 (2004).
Mukoyama et al., Augmented secretion of brain natriuretic peptide in acute myocardial infarction. Biochem Biophys Res Commun. 180(1):431-6 (1991). (Abstract Only).
Murphy et al., "Signaling and transcription in T helper development," Annu. Rev. Immunol. 18:451-94 (2000).
Murray et al. "Chronic beta-adrenergic stimulation induces myocardial proinflammatory cytokine expression," Circulation, May 23, 2000, 101(20):2338-41.
MX Office Action in Mexican Appln. No. MX/a/2015/002254, dated Feb. 24, 2020, 9 pages (with English translation).
MX Office Action in Mexican Appln. No. MX/a/2015/002254, dated Oct. 1, 2019, 8 pages (with English translation).
Nakano et al., "Characterization of Soluble Thrombomodulin Fragments in Human Urine," Thrombosis and Haemostasis, Jan. 31, 1998, 79(2):331-337.
Nakano et al., "Elevation of Soluble Thrombomodulin Antigen Levels in the Seram and Urine of Streptozotocin-Induced Diabetes Model Rats," Thrombosis Research Jul. 1, 2000, 99:83-91.
NCBI Blastn 2.0.14, Jun. 29, 2000, BLAST Results, 2065 letters, printed Aug. 23, 2000, 5 pages.
NCBI Blastn 2.2.2, Blast Results, 1011 Letters, Dec. 14, 2001, 21 pages.
NCBI Blastn 2.2.2, Blast Results, 336 Letters, Dec. 14, 2001, 15 pages.
Ng et al., "Diagnosis of heart failure using urinary natriuretic peptides," Clin. Sci. (Lond). 106(2): 129-33 (2004).
Nichols et al., "The influence of 'diastolic' length on the contractility of isolated cat papillary muscle," The Journal of Physiology, Apr. 1, 1985, 361:269-79.
Nozaki et al., "Soluble Tumor Necrosis Factor Receptors are Elevated in Relation to Severity of Congestive Heart Failure," Jpn. Ciro. J. 61:657-64 (1997).
O'Neill et al., "The IL-1 receptor/toll-like receptor superfamily: crucial receptors for inflammation and host defense," Immunol. Today. 21(5):206-9 (2000).
Oh et al., "Diastolic Heart Failure Can Be Diagnosed by Comprehensive Two-Dimensional and Doppler Echocardiography," Journal of American College of Cardiology, Feb. 7, 2006, 47:500-506.

Ohki et al., "Identification of mechanically induced genes in human monocytic cells by DNA microarrays," Journal of Hypertension, Apr. 1, 2002, 20(4):685-691.
Ohtsuka et al., "Effect of beta-blockers on circulating levels of inflammatory and anti-inflammatory cytokines in patients with dilated cardiomyopathy," J. Am. Coll. Cardiol. 37(2):412-7 (2001).
Onda et al., "Identification of Genes Differentially Expressed in Canine Vasospastic Cerebral Arteries After Subarachnoid Hemorrhage," Journal of Cerebral Blood Flow & Metabolism, Nov. 1999, 19:1279-1288.
O'Neill et al., "The IL-1 receptor/toll-like receptor superfamily: crucial receptors for inflammation and host defense." Immunology Today, May 2000. 21(5):206-9.
Ordonez-Llanos et ah, "A formula combining ST2 and NT-proBNP enhances prognostic accuracy in patients with heart failure," Clinical Chemistry, Jun. 1, 2008, 54(6):A99, 6 pages.
ørntoft et al., "Genome-wide study of gene copy numbers, transcripts, and protein levels in pairs of non-invasive and invasive human transitional cell carcinomas," Molecular & Cellular Proteomics, Jan. 1, 2002, 1(1):37-45.
Oras et al., "Prognostic Value of Serum Cytokines in Patients with Congestive Heart Failure," J. Heart Lung Transplant, 2000, 19:419-25.
Oshikawa et al., "Acute eosinophilic pneumonia with increased soluble ST2 in serum and bronchoalveolar lavage fluid," Respir. Med., 95(6):532-533 (2001).
Oshikawa et al., "Elevated Soluble ST2 Protein Levels in Sera of Patients with Asthma with an Acute Exacerbation," Am. J. Respir. Crit. Care Med. 164:277-281 (2001).
Oshikawa et al., "Expression and function of the ST2 gene in a murine model of allergic airway inflammation," Clin. Exp. Allergy, 32(10): 1520-1526 (2002).
Oshikawa et al., "Expression of ST2 in helper T lymphocytes of malignant pleural effusions," Am. J. Respir. Crit. Care Med., 165(7):1005-1009 (2002).
Oshikawa et al., "ST2 protein induced by inflammatory stimuli can modulate acute lung inflammation," Biochem. Biophys. Res, Commun. 299(1): 18-24 (2002).
Papetropoulos et al., "Nitric oxide synthase inhibitors attenuate transforming-growth-factor-beta 1-stimulated capillary organization in vitro," American Journal of Pathology, May 1997, 150(5):1835-44.
PCT International Preliminary Report on Patentability for International Appln. No. PCT/US2013/056020 dated Feb. 24, 2015, 7 pages.
PCT International Preliminary Report on Patentability for PCT/US2007/067333, dated Oct. 28, 2008, 6 pages.
PCT International Preliminary Report on Patentability for PCT/US2009/040941, dated Oct. 19, 2010.
PCT International Preliminary Report on Patentability in International Appln. No. PCT/US07/068024, dated Sep. 9, 2008, 5 pages.
PCT International Preliminary Report on Patentability in International Appln. No. PCT/US2001/046816, dated Aug. 16, 2004, 4 pages.
PCT International Preliminary- Report on Patentability in International Appln. No. PCT/US2007/067626, dated Nov. 6, 2008, 6 pages.
PCT International Preliminary Report on Patentability in International Appln. No. PCT/US2007/067914, dated Nov. 4, 2008, 6 pages.
PCT International Search Report and Written Opinion in International Appln. No. PCT/US2003/14882 dated Feb. 9, 2005, 1 page.
PCT International Search Report and Written Opinion in International Appln. No. PCT/US2009/040941, dated Dec. 3, 2009, 3 pages.
PCT International Search Report and Written Opinion in International Appln. No. PCT/US2007/067626, dated Aug. 5, 2008, 7 pages.
PCT International Search Report and Written Opinion in International Appln. No. PCT/USO1/46816 dated May 9, 2003, 5 pages.
PCT International Search Report and Written Opinion in International Appln. No. PCT/US2007/010925, dated Apr. 18, 2008, 11 pages.

(56) References Cited

OTHER PUBLICATIONS

PCT International Search Report and Written Opinion in International Appln. No. PCT/US2007/067333, dated Jan. 23, 2008, 7 pages.
PCT International Search Report and Written Opinion in International Appln. No. PCT/US2013/056020 dated Dec. 12, 2013, 11 pages.
PCT ISR as issued in PCT/US2007/067333 on Jan. 23, 2008.
PCT Written Opinion of the International Searching Authority in International Appln. No. PCT/US2007/067914, dated Jul. 22, 2008, 28 pages.
Perrier et al., "D-dimer testing for suspected pulmonary embolism in outpatients," Am. J. Respir. Crit. Care Med., 156(2):492-496 (1997).
Porela et al., "Prediction of Short-Term Outcome in Patients With Suspected Myocardial Infarction," Annals of Emergency Medicine, May 2000, 35(5):413-420.
Potter el al., "Mutations in the murine fitness 1 gene result in defective hematopoiesis." Blood, 90(5):1850-7 (1997).
Prabhu et al., "beta-adrenergic blockade in developing heart, failure: effects on myocardial inflammatory cytokines, nitric oxide, and remodeling," Circulation, May 2, 2000, 101(17):2103-9.
Pulkki, "Cytokines and cardiomyocyte death," Annals of Medicine, Jan. 1, 1997, 29(4):339-43.
Richards et al., "Plasma N-terminal pro-brain natriuretic peptide and adrenomedullin: new neurohormonal predictors of left ventricular function and prognosis after myocardial infarction." Circulation, 97:1921-1929 (1998).
Ridker et al., "Inflammation, Aspirin, And The Risk Of Cardiovascular Disease In Apparently Healthy Men," New England J. Med., 336:973-979 (1997).
Ridker et al.," C-reactive protein and other markers of inflammation in the prediction of cardiovascular disease in women," N. Engl. J. Med., 324: 836-843 (2000).
Rohde et al., "Circulating Cell Adhesion Molecules Are Correlated With Ultrasound-Based Assessment of Carotid Atherosclerosis," Arterial Sclerotic Vasc. Biol., 18:1765-1770 (1998).
Rohde et al., "Plasma Concentrations of Interleukin-6 and Abdominal Aortic Diameter Among Subjects Without Aortic Dilatation," Arterial Sclerotic Vasc. Biol., 19:1695-1699 (1999).
Roig et al., "Serum interleukin-6 in congestive heart failure secondary to idiopathic dilated cardiomyopathy," Am. J. Cardiol. 82(5):688-90, A8 (1998).
RU Office Action in Russian Appln. No. 2015110054, dated Jun. 7, 2018, 16 pages (with English translation).
RU Russian Office Action in Appln. No. 2015110054, dated Jun. 21, 2017, 15 pages (with English translation).
Sabatine et al., "Complementary Roles for Biomarkers of Biomechanical Strain ST2 and N-Terminal Prohormone B-Type Natriuretic Peptide in Patients With ST-Elevation Myocardial Infarction", Circulation, 117(15): 1936-1944 (2008).
Sabatine et al., "Multimarker approach to risk stratification in non-ST elevation acute coronary syndromes: simultaneous assessment, of troponin I, C-reactive protein, and B-type natriuretic peptide," Circulation, 105(15): 1760-1763 (2002).
Saccani et al., "Divergent effects of LPS on expression of IL-receptor family members in mononuclear phagocytes in vitro and in vivo," Cytokine, 10(10): 773-80 (1998).
Schaffer et al., "Device for the Application of a dynamic biaxially uniform and isotropic strain to a flexible cell culture membrane," Journal of Orthopaedic Research, Sep. 1994, 12(5):709-19.
Schmitz et al., "IL-33, an interleukin-1-like cytokine that signals via the IL-1 receptor-related protein ST2 and induces T helper type 2-associated cytokines," Immunity, 23(5):479-490 (2005).
Selvais et al., "Direct, comparison between endothelin-1, N-terminal proatrial natriuretic factor, and brain natriuretic peptide as prognostic markers of survival in congestive heart, failure," J. Card. Fail., 6(3):201-7 (2000). (Abstract Only).
SG Office Action in Singapore Appln. No. 11201501271T, dated Jan. 2, 2016, 11 pages.
SG Office Action in Singaporean Appln. No. 10201608854T, dated Jun. 22, 2020, 9 pages.
SG Singapore Office Action in Singapore Appln. No. 11201501271T, 12 pages, dated Aug. 6, 2016.
Shimizu et al., "Functional SNPs in the distal promoter of the ST2 gene are associated with atopic dermatitis," Human Molecular Genetics, Aug. 23, 2005, 14(19):2919-2927.
Shimpo et al., "Serum levels of the interleukin-1 receptor family member ST2 predict, mortality and clinical outcome in acute myocardial infarction" Circulation, 109(18):2186-2190 (2004).
Silver et ah. "BNP Consensus Panel 2004: A clinical approach for the diagnostic, prognostic. screening, treatment monitoring, and therapeutic roles of natriuretic peptides in cardiovascular diseases," Congest. Heart Fail., 10(5 suppl. 3):1-30 (2004).
Sims, "IL-1 and IL-18 Receptors, and Their Extended Family," Current Opinion in Immunology, Feb. 1, 2002; 14:117-122.
Strunk et al., "Impact of the history of congestive heart failure on the utility of B-type natriuretic peptide in the emergency diagnosis of heart failure: results from the Breathing Not Properly Multinational Study," The American Journal of Medicine, Jan. 1, 2006, 119(1):69-e1.
Sussman et al., "Dance band on the Titanic: biomechanical signaling in cardiac hypertrophy," Circulation Research, Nov. 15, 2002, 91(10):888-98.
Sutton et al., "Left ventricular remodeling after myocardial infarction: pathophysiology and therapy," Circulation, Jun. 27, 2000, 101(25):2981-8.
Svensson et al., "Prognostic value of biochemical markers, 12-lead ECG and patient characteristics amongst patients calling for an ambulance due to a suspected acute coronary syndrome," Journal of Internal Medicine, Apr. 2004, 255(4):469-77.
Tajima et al., "The increase in serum soluble ST2 protein upon acute exacerbation of idiopathic pulmonary fibrosis," Chest, Oct. 1, 2003, 124(4):1206-14.
Tang et al., "Gene expression profiling during the transition to failure in TNF-α over-expressing mice demonstrates the development of autoimmune myocarditis," Journal of Molecular and Cellular' Cardiology, Apr. 1, 2004, 36(4):515-30.
Tominaga et al., "A putative protein of a growth specific cDNA from BALB/c-3T3 cells is highly similar to the extracellular portion of mouse interleukin 1 receptor," FEBS Letters, Dec. 4, 1989, 258(2):301-4.
Tominaga et al., "Nucleotide sequence of a complementary DNA for humans ST2," Biochimica et Biophysica Acta (BBA)-Gene Structure and Expression, Dec. 29, 1992, 1171(2):215-8.
Tominaga et al., "The existence of a growth-specific DNA binding factor for the promoter region of mouse ST2 gene," FEBS Letters, Nov. 14, 1994, 354(3):311-4.
Tominaga et al., "ST2 gene: a gene that is induced by growth stimulation and encoding a product highly similar to the interleukin 1 receptors." Seikasaku. 67(5):356-64 (1995). Review. Japanese with translation.
Townsend et al., "T1/ST2-deficient mice demonstrate the importance of T1/ST2 in developing primary T helper cell type 2 responses," Journal of Experimental Medicine. Mar. 2000. 20; 191(6):1069-1076.
Trehu et al., "Phase I trial of interleukin 2 in combination with the soluble tumor necrosis factor receptor p75 IgG chimera," Clinical Cancer Research, Aug. 1, 1996, 2(8):1341-51.
Tsuchiya et al., "Th, Th2 and activated T-cell marker and clinical prognosis in peripheral T-cell lymphoma unspecified comparison AILD, ALCL, lymphoblastic lymphoma and ATLL," Blood, 103:236-241 (2004).
Tsutamoto et al., "Interleukin-6 spillover in the peripheral circulation increases with the severity of heart failure, and the high plasma level of interleukin-6 is an important prognostic predictor in patients with congestive heart failure," Journal of the American College of Cardiology, Feb. 1998, 31(2):391-8.
Tung et al., "Amino-terminal pro-brain natriuretic peptide for the diagnosis of acute heart failure in patients with previous obstructive airway disease," Annals of Emergency Medicine. Jul. 1, 2006, 48(1):66-74.

(56) References Cited

OTHER PUBLICATIONS

Tung et al., "Influence of stretch on excitation threshold of single frog ventricular cells," Experimental Physiology, Mar. 1, 1995, 80(2):221-35.
Tung et al., "Utility of B-type natriuretic peptide for the evaluation of intensive care unit shock," Critical Care Medicine, Aug. 1, 2004, 32(8):1643-1647.
U.S. Amendment Filed in Response to Office Action in U.S. Appl. No. 10/024,607, dated May 30, 2006, 20 pages.
U.S. Amendment in Reply to Office Action in U.S. Appl. No. 13/179,173, dated Jul. 1, 2013, 16 pages.
U.S. Amendment in Reply to Office Action in U.S. Appl. No. 13/179,173, dated Feb. 11, 2013, 8 pages.
U.S. Amendment in Response to Office Action in U.S. Appl. No. 13/179,173, dated Nov. 15, 2011, 2 pages.
U.S. Amendment in Response to Office Action in U.S. Appl. No. 13/179,173, dated Jul. 18, 2012, 8 pages.
U.S. Interview Summary in U.S. Appl. No. 10/024,607, dated Nov. 23, 2005, 3 pages.
U.S. Notice of Allowance in U.S. Appl. No. 10/435,482, dated Jul. 5, 2007, 9 pages.
U.S. Notice of Allowance in U.S. Appl. No. 10/435,482, dated Apr. 3, 2007, 6 pages.
U.S. Notice of Allowance in U.S. Appl. No. 10/435,482, dated Oct. 3, 2007, 6 pages.
U.S. Notice of Allowance in U.S. Appl. No. 13/179,173, dated Aug. 26, 2013, 6 pages.
U.S. Office Action in U.S. Appl. No. 10/024,607, dated Jul. 27, 2006, 15 pages.
U.S. Office Action in U.S. Appl. No. 10/024,607, dated Mar. 29, 2006, 12 pages.
U.S. Office Action in U.S. Appl. No. 10/024,607, dated Oct. 7, 2005, 13 pages.
U.S. Office Action in U.S. Appl. No. 10/435,482, dated Mar. 10, 2009, 27 pages.
U.S. Office Action in U.S. Appl. No. 10/435,482, dated May 2, 2008, 37 pages.
U.S. Office Action in U.S. Appl. No. 10/435,482, dated Oct. 18, 2006, 9 pages.
U.S. Office Action in U.S. Appl. No. 11/441,780, dated Mar. 26, 2008, 14 pages.
U.S. Office Action in U.S. Appl. No. 11/789,169, dated Mar. 4, 2009, 11 pages.
U.S. Office Action in U.S. Appl. No. 11/789,169, dated Dec. 17, 2009, 10 pages.
U.S. Office Action in U.S. Appl. No. 11/789,169, dated Nov. 14, 2008, 11 pages.
U.S. Office Action in U.S. Appl. No. 11/789,169, dated, Jul. 9, 2009, 7 pages.
U.S. Office Action in U.S. Appl. No. 12/167,143, dated Apr. 5, 2010, 7 pages.
U.S. Office Action in U.S. Appl. No. 12/167,143, dated Oct. 15, 2010, 5 pages.
U.S. Office Action in U.S. Appl. No. 12/298,613, dated May 14, 2010, 10 pages.
U.S. Office Action in U.S. Appl. No. 13/150,749, dated Jun. 20, 2013, 4 pages.
U.S. Office Action in U.S. Appln. No. 13/150,749, dated Mar. 7, 2013, 8 pages.
U.S. Office Action in U.S. Appl. No. 13/151,012, dated May 24, 2012, 6 pages.
U.S. Office Action in U.S. Appl. No. 13/151,012, dated Nov. 5, 2012, 6 pages.
U.S. Office Action in U.S. Appl. No. 13/179,173, dated Oct. 21, 2011, 8 pages.
U.S. Office Action in U.S. Appl. No. 13/179,173, dated Mar. 1, 2013, 8 pages.
U.S. Office Action in U.S. Appl. No. 13/179,173, dated Jan. 19, 2012, 18 pages.
U.S. Office Action in U.S. Appl. No. 13/179,173, dated Oct. 26, 2012, 10 pages.
U.S. Office Action in U.S. Appl. No. 13/179,173, dated Sep. 23, 2011, 7 pages.
U.S. Office Action in U.S. Appl. No. 13/282,111, dated Apr. 4, 2012, 9 pages.
U.S. Office Action in U.S. Appl. No. 13/282,111, dated Apr. 21, 2015, 9 pages.
U.S. Office Action in U.S. Appl. No. 13/282,111, dated Feb. 2, 2016, 9 pages.
U.S. Office Action in U.S. Appl. No. 13/282,111, dated Jan. 27, 2014, 5 pages.
U.S. Office Action in U.S. Appl. No. 13/282,111, dated Nov. 19, 2012, 8 pages.
U.S. Office Action in U.S. Appl. No. 13/787,137, dated Apr. 6, 2017, 6 pages.
U.S. Office Action in U.S. Appl. No. 13/787,975, dated Sep. 12, 2016, 17 pages.
U.S. Office Action in U.S. Appl. No. 13/787,975, dated Dec. 30, 2013, 6 pages.
U.S. Office Action in U.S. Appl. No. 13/787,975, dated Jul. 23, 2014, 9 pages.
U.S. Office Action in U.S. Appl. No. 13/788,276, dated Sep. 18, 2013, 8 pages.
U.S. Office Action in U.S. Appl. No. 13/789,941, dated Dec. 11, 2013, 15 pages.
U.S. Office Action in U.S. Appl. No. 13/789,941, dated Sep. 18, 2013, 8 pages.
U.S. Office Action in U.S. Appl. No. 14/244,526, dated Aug. 30, 2016, 14 pages.
U.S. Office Action in U.S. Appl. No. 14/312,221, dated Sep. 20, 2016, 39 pages.
U.S. Office Action in U.S. Appl. No. 14/523,694, dated Jan. 12, 2016, 13 pages.
U.S. Office Action in U.S. Appl. No. 14/290,465, dated Jan. 30, 2017, 17 pages.
U.S. Office Action in U.S. Appl. No. 14/312,221, dated Jan. 25, 2018, 46 pages.
U.S. Prosecution File History for U.S. Appl. No. 11/789,169 do+A179wnloaded from U.S. Patent and Trademark Office website on Jul. 1, 2013, first document 150 pages, second document 146 pages.
U.S. Prosecution File History for U.S. Appln, No. 12/425,956 downloaded from U.S. Patent and Trademark Office website on Jul. 1, 2013, 111 pages.
U.S. Prosecution File History for U.S. Appl. No. 13/151,012, downloaded from U.S. Patent and Trademark Office website on Jul. 1, 2013, 212 pages.
U.S. Prosecution File History for U.S. Appl. No. 13/282,111, downloaded from U.S. Patent and Trademark Office website on Jul. 1, 2013, 195 pages.
U.S. Prosecution File History for U.S. Appl. No. 13/422,574 downloaded from U.S. Patent and Trademark Office website on Jul. 1, 2013, 62 pages.
U.S. Prosecution File History for U.S. Appl. No. 13/422,574 downloaded from U.S. Patent and Trademark Office website on Jul. 1, 2013, 122 pages.
U.S. Response to Office Action in U.S. Appl. No. 10/024,607, dated Dec. 23, 2005, 24 pages.
U.S. Response to Office Action in U.S. Appl. No. 12/167,143, dated Oct. 19, 2006, 9 pages.
U.S. Response to Office Action in U.S. Appl. No. 12/167,143, dated Jul. 6, 2010, 9 pages.
U.S. Response to Office Action in U.S. Appl. No. 12/167,143, dated Nov. 24, 2010, 3 pages.
U.S. Response to Office Action in U.S. Appl. No. 13/151,012, dated Feb. 5, 2013, 15 pages.
U.S. Response to Office Action in U.S. Appl. No. 13/151,012, dated Jan. 23, 2012, 3 pages.
U.S. Response to Office Action in U.S. Appl. No. 13/151,012, dated Sep. 24, 2012, 2 pages.
U.S. Response to Restriction Requirement in U.S. Appl. No. 12/167,143, dated Feb. 16, 2010, 6 pages.

(56) References Cited

OTHER PUBLICATIONS

U.S. Response to Restriction Requirement in U.S, U.S. Appl. No. 12/298,613, dated Apr. 12, 2010, 1 page.
U.S. Response to Restriction Requirement in U.S. Appl. No. 12/614,970, dated Oct. 27, 2010, 1 page.
U.S. Response to Restriction Requirement in U.S. Appl. No. 13/788,276, dated Aug. 30, 2013, 1 page.
U.S. Restriction Requirement in U.S. Appl. No. 10/435,482, dated Jun. 30, 2005, 9 pages.
U.S. Restriction Requirement in U.S. Appl. No. 10/435,482, dated Apr. 17, 2006, 14 pages.
U.S. Restriction Requirement in U.S. /U.S. Appl. No. 10/435,482, dated Jun. 27, 2006, 6 pages.
U.S. Restriction Requirement in U.S. Appl. No. 12/167,143, dated Nov. 16, 2009, 10 pages.
U.S. Restriction Requirement in U.S. Appl. No. 12/614,970, dated Mar. 10, 2010, 8 pages.
U.S. Restriction Requirement in U.S. Appl. No. 12/614,970, dated Sep. 28, 2010, 4 pages.
U.S. Restriction Requirement in U.S. Appl. No. 13/150,749, dated Aug. 20, 2012, 4 pages.
U.S. Restriction Requirement in U.S. Appl. No. 13/788,276, dated Jul. 30, 2013, 4 pages.
U.S. Restriction Requirement in U.S. Appl. No. 13/789,941, dated Aug. 2, 2013, 5 pages
Vahl et al., "Length dependence of calcium—and force-transients in normal and failing human myocardium," Journal of Molecular and Cellular Cardiology, May 1, 1998, 30(5):957-66.
Van Kimmenade et al., "Utility of amino-terminal pro-brain natriuretic peptide, galectin-3, and apelin for the evaluation of patients with acute heart failure," Journal of the American College of Cardiology, Sep. 2006, 19;48(6): 1217-24.
Vidal et al., "Prognostic Value of Cytokines and Neurohormones in Severe Heart Failure, "Revista Espanola de Cardiologia, 2002, 55(5):481-6.
Wang et al., "Expression of interleukin-1β, interleukin-1 receptor, and interleukin-1 receptor antagonist mRNA in rat carotid artery after balloon angioplasty." Biochemical and Biophysical Research Communications, Apr. 29, 2000. 271(1): 138-43
Webmd.com' [online], "Meditation May Benefit Heart Patients," Mar. 2007, Retrieved from the internet: URL <https://www.webmd.com/heart-disease/heart-failure/news/20070307/meditation-may-benefit-heart-patients#1>. 2 pages.
Weinberg et al., "Expression and regulation of ST2, an intereukin-1 receptor family member, in cardiomyocytes and myocardial infarction," Circulation, Dec. 3, 2002, 106(23):2961-6.
Weinberg et al., "Identification of serum soluble ST2 receptor as a novel heart failure biomarker," Circulation, Feb. 11, 2003. 107(5):721-6.
Yamamoto et al., "Induction of tenascin-C in cardiac myocytes by mechanical deformation role of reactive oxygen species." Journal of Biological Chemistry, Jul. 30, 1999, 274(31):21840-6.
Yamamoto et al., "Mechanical strain suppresses inducible nitric-oxide synthase in cardiac myocytes," Journal of Biological Chemistry, May 8, 1998, 273(19): 11862-6.
Yamamoto et al., "Regulation of cardiomyocyte mechanotransduction by the cardiac cycle," Circulation, Mar. 13, 2001, 103(10): 1459-64.
Yamaoka et al., "Anti-inflammatory cytokine profile in human heart failure: behavior of interleukin-10 in association with tumor necrosis factor-alpha," Japanese Circulation Journal, Dec. 1999, 63(12):951-956.
Yanagisawa et al., "Murine ST2 gene is a member of the primary response gene family induced by growth factors," FEBS Letters, May 4, 1992, 302(1):51-3.
Yanagisawa et al., "Presence of a novel primary response gene ST2L, encoding a product highly similar to the interleukin 1 receptor type 1," FEBS Letters, Feb. 22, 1993, 318(1):83-7.
Yanagisawa et al., "The expression of ST2 gene in helper T cells and the binding of ST2 protein to myeloma-derived RPMI8226 cells," The Journal of Biochemistry, Jan. 1, 1997, 121(1):95-103.
Yasue et al., "Localization and mechanism of secretion of B-type natriuretic peptide in comparison with those of A-type natriuretic peptide in normal subjects and patients with heart failure," Circulation, Jul. 1994, 90(1): 195-203.
Zebrack et al., "Usefulness of high-sensitivity C-reactive protein in predicting long-term risk of death or acute myocardial infarction in patients with unstable or stable angina pectoris or acute myocardial infarction," Am Journal of Cardiology, Jan. 2002, 15:89(2):145-9.

\* cited by examiner

| Area under the ROC curve (AUC) | 0.800 |
| Standard error | 0.0637 |
| 95% Confidence interval | 0.659 to 0.901 |
| Significance level P (Area=0.5) | 0.0001 |

Criterion values and coordinates of the ROC curve

| Criterion | Sensitivity | 95% CI | Specificity | 95% CI | +LR | -LR |
|---|---|---|---|---|---|---|
| >=2 | 100.00 | 86.7 - 100.0 | 0.00 | 0.0 - 15.6 | 1.00 | |
| >2.5 | 100.00 | 86.7 - 100.0 | 13.64 | 3.1 - 34.9 | 1.16 | 0.00 |
| >2.6 | 96.15 | 80.3 - 99.4 | 18.18 | 5.3 - 40.3 | 1.18 | 0.21 |
| >2.8 | 96.15 | 80.3 - 99.4 | 27.27 | 10.8 - 50.2 | 1.32 | 0.14 |
| >2.9 | 92.31 | 74.8 - 98.8 | 31.82 | 13.9 - 54.9 | 1.35 | 0.24 |
| >3 | 92.31 | 74.8 - 98.8 | 50.00 | 28.2 - 71.8 | 1.85 | 0.15 |
| >3.1 | 88.46 | 69.8 - 97.4 | 63.64 | 40.7 - 82.8 | 2.43 | 0.18 |
| >3.2 | 84.62 | 65.1 - 95.5 | 68.18 | 45.1 - 86.1 | 2.66 | 0.23 |
| >3.3 * | 80.77 | 60.6 - 93.4 | 72.73 | 49.8 - 89.2 | 2.96 | 0.26 |
| >3.6 | 53.85 | 33.4 - 73.4 | 72.73 | 49.8 - 89.2 | 1.97 | 0.63 |
| >3.7 | 50.00 | 29.9 - 70.1 | 77.27 | 54.6 - 92.1 | 2.20 | 0.65 |
| >3.9 | 50.00 | 29.9 - 70.1 | 81.82 | 59.7 - 94.7 | 2.75 | 0.61 |
| >4 | 46.15 | 26.6 - 66.6 | 81.82 | 59.7 - 94.7 | 2.54 | 0.66 |
| >4.1 | 42.31 | 23.4 - 63.1 | 90.91 | 70.8 - 98.6 | 4.65 | 0.63 |

MACERS

| Area under the ROC curve (AUC) | 0.766 |
| Standard error | 0.0734 |
| 95% Confidence interval | 0.621 to 0.876 |
| Significance level P (Area=0.5) | 0.0003 |

Criterion values and coordinates of the ROC curve

| | | | | | | |
|---|---|---|---|---|---|---|
| >3.1 | 89.47 | 66.8 - 98.4 | 51.72 | 32.5 - 70.5 | 1.85 | 0.20 |
| >3.2 | 84.21 | 60.4 - 96.4 | 55.17 | 35.7 - 73.5 | 1.88 | 0.29 |
| >3.3 | 84.21 | 60.4 - 96.4 | 62.07 | 42.3 - 79.3 | 2.22 | 0.25 |
| >3.4 | 78.95 | 54.4 - 93.8 | 62.07 | 42.3 - 79.3 | 2.08 | 0.34 |
| >3.5 * | 78.95 | 54.4 - 93.8 | 68.97 | 49.2 - 84.7 | 2.54 | 0.31 |
| >3.6 | 63.16 | 38.4 - 83.6 | 72.41 | 52.8 - 87.2 | 2.29 | 0.51 |
| >3.7 | 57.89 | 33.5 - 79.7 | 75.86 | 56.5 - 89.7 | 2.40 | 0.56 |
| >3.9 | 57.89 | 33.5 - 79.7 | 79.31 | 60.3 - 92.0 | 2.80 | 0.53 |
| >4 | 52.63 | 28.9 - 75.5 | 79.31 | 60.3 - 92.0 | 2.54 | 0.60 |

PREDICTING RISK OF MAJOR ADVERSE CARDIAC EVENTS

CLAIM OF PRIORITY

This application is a continuation application of U.S. patent application Ser. No. 14/244,526, filed on Apr. 3, 2014 (issued as U.S. Pat. No. 9,965,593), which is a continuation application of U.S. patent application Ser. No. 13/787,137, filed on Mar. 6, 2013 (issued as U.S. Pat. No. 9,886,553), which is a continuation application of U.S. patent application Ser. No. 13/299,612, filed on Nov. 18, 2011, which is a continuation application of U.S. patent application Ser. No. 12/425,956, filed on Apr. 17, 2009 (issued as U.S. Pat. No. 8,090,562), which claims the benefit of U.S. Provisional Patent Application Ser. No. 61/046,158, filed on Apr. 18, 2008; the entire contents of each of the foregoing applications are hereby incorporated by reference.

TECHNICAL FIELD

The invention relates to methods for predicting risk of major adverse cardiac events and detecting the presence of severe disease based on circulating levels of ST2 and natriuretic peptides (NP), e.g., NT-proBNP, alone or in combination with other biomarkers.

BACKGROUND

Clinical evaluation for determination of disease severity and risk of major adverse cardiac events (MACE), e.g., mortality due to heart failure, may not always be apparent. The decision whether to treat a subject aggressively or conservatively, or to admit the subject as an inpatient or to send them home, may sometimes be made solely on a physician's clinical assessment or "gut feeling" as to the individual's actual condition. A formula for determining a subject's likelihood of an adverse outcome, e.g., mortality, transplantation, and/or readmission, would significantly enhance the physician's ability to make informed treatment decisions, improve patient care and reduce overall healthcare costs.

SUMMARY

The present invention is based, at least in part, on the use of changes in serum levels of the biomarker ST2 (Growth Stimulation-Expressed Gene 2, also known as Interleukin 1 Receptor Like 1 (IL1RL-1)), in combination with levels of a natriuretic peptide (NP) such as the inactive N-terminal fragment of brain-type natriuretic peptide (NT-pro-BNP), to predict the likelihood of a major adverse cardiac event (MACE), e.g., recurrence of the initial cardiac event (e.g., a second MI); angina; decompensation of heart failure; admission for cardiovascular disease (CVD); mortality due to CVD; or transplant, within a specific time period, e.g., 30 days, 3 or 6 months, or a year or more, or to detect the presence of severe disease (e.g., severe disease likely to require transplantation or other aggressive treatment). These methods can be used to predict clinical outcome, e.g., in patients hospitalized after an acute cardiac event.

In some embodiments, the methods described herein include monitoring changes in ST2 levels over time (e.g., an ST2 ratio) and determining an NP level, to provide diagnostic and prognostic evaluation of patients, e.g., patients with non-specific symptoms, e.g., acutely dyspneic patients and those with chest pain, or patients who have been diagnosed with heart failure. NPs include the forms of the brain natriuretic peptides, i.e., NT-proBNP, proBNP, and BNP, and the atrial natriuretic peptides, i.e., NT-proANP, proANP, and ANP. In preferred embodiments, the NP is NT-proBNP.

In some embodiments, the invention features methods for evaluating the risk of a MACE within a specific time period, e.g., 30, 60, 90, or 180 days (e.g., one, two, three, or six months), or one, two, or five years, for a subject. The methods can include determining ratios of ST2 and a level of an NP, e.g., NT-proBNP, and using those ratios and levels to determine risk of MACE, as described herein. Determining a ratio of ST2 can include obtaining at least two samples, e.g., samples of blood, serum, plasma, urine, or body tissue from the subject (both samples are from the same fluid or tissue, taken at two different time points); determining levels of ST2 in the samples; and dividing the biomarker levels of ST2 in the earlier samples into the levels of ST2 in the later sample, thereby arriving at a ratio of ST2. Such a ratio provides an indication of how the levels of ST2 are changing in the subject over time. Thus, in some embodiments, the methods include determining or obtaining a first ST2 level, e.g., a baseline level in a sample taken, e.g., at admission or at initiation of treatment, and a second ST2 level, e.g., in a sample taken some time later, e.g., one, two, three, four, or more days later. In addition, the methods will generally include determining or obtaining an NP level, e.g., an NT-proBNP level at least at the second time point, e.g., in a sample of blood, serum, plasma, urine, or body tissue from the subject.

In one aspect, the invention provides methods, e.g., computer-implemented methods, for evaluating the risk of a major adverse cardiac event (MACE) for a subject within one year. The methods include determining a MACE risk score (MACERS) for a subject based upon, at least in part, the ratio of a second level of Growth Stimulation-Expressed Gene 2 (ST2) in the subject at a second time (ST2 T0) to a first level of ST2 in the subject at a first time (ST2 T1), in combination with a weighted logarithm of a level of a natriuretic peptide (NP) in the subject at the second time (NP T1), and comparing the MACERS to a reference MACERS; wherein the MACERS in comparison with the reference MACERS indicates the subject's risk of a MACE within one year.

In some embodiments, the methods described herein include the use of the following formula to determine a subject's risk of a MACE:

$$X = (ST2\ T1/ST2\ T0) + \alpha\ \ln(NP\ T1)$$

In preferred embodiments, the ST2 ratios and NT-proBNP levels, are used to determine a MACE risk score using the following formula:

$$X = (ST2\ T1/ST2\ T0) + \alpha\ \ln(NTproBNP\ T1)$$

In some embodiments, the coefficient alpha is 0.33.

In some embodiments, the subject's MACE risk score is compared to a reference MACE risk score (e.g., a threshold value). A comparison of the subject's MACE risk score versus the reference score indicates the subject's risk of a MACE within the specific time period. In some embodiments, the specific time period is one year.

In some embodiments, the reference MACE risk score represents the score in a subject or group of subjects who have a low risk of death within one year. In some embodiments, a subject MACE risk score that is greater than or equal to the reference MACE risk score indicates that the subject has an elevated, i.e., statistically significantly elevated, risk of death within one year. In some embodiments, the elevated risk of death is at least 20% higher, e.g., 30%, 40%, or 50% higher.

In some embodiments, the methods include determining a MACE risk score, and optionally selecting or modifying a treatment for the subject, based on the MACE risk score. For example, if the MACE risk score is more than a selected reference, then the subject has a high risk and should be treated more aggressively; if the subject is already being treated, then the subject is not responding favorably to the current treatment and a new treatment should be selected, i.e., an alternate treatment to which the patient may respond more favorably.

In some embodiments, the subject exhibits one or more non-specific symptoms, e.g., chest pain or discomfort, shortness of breath (dyspnea), nausea, vomiting, eructation, sweating, palpitations, lightheadedness, fatigue, and fainting. In some embodiments, the symptom is dyspnea or chest pain.

In some embodiments, the subject does not have a cardiovascular disorder. In various embodiments, the subject has a pulmonary disorder, e.g., acute infection (e.g., pneumonia), chronic obstructive pulmonary disease (COPD), and pulmonary embolism.

In certain embodiments, the subject has a liver disorder, e.g., a liver disorder associated with chemotherapy, alcohol toxicity, or drug toxicity as determined by standard liver function laboratory tests.

In some embodiments, the methods further include determining the level of an adjunct (non-ST2, non-IL-33, non-NT-proBNP) biomarker, e.g., Troponin, CRP, D-dimers, BUN, albumin, liver function enzymes, measures of renal function, e.g., creatinine, creatinine clearance rate, or glomerular filtration rate, and/or bacterial endotoxin, in the sample; and comparing the level of the adjunct biomarker in the sample to a reference level of the adjunct biomarker. The level of the adjunct biomarker in the sample as compared to the reference, in combination with the MACE risk score in the sample as compared to a reference MACE risk score, indicates whether the subject has an elevated risk of death within a specific time period, and/or has a present severe disease. In some embodiments, the methods include determining a change in levels over time (e.g., a ratio) for the adjunct biomarker, by comparing a first level, e.g., a baseline level, to a second level, e.g., a level taken some time later, e.g., one, two, three, four, or more days later.

In some embodiments, the subject has a BMI of 25-29, a BMI of ≥30, or renal insufficiency, e.g., the subject is selected on the basis that they have a BMI of 25-29, a BMI of ≥30, or renal insufficiency.

In another aspect, the invention includes methods for evaluating a subject's condition over time, e.g., for evaluating the efficacy of a treatment in a subject. The methods include determining a first MACE risk score in a subject, based upon a ratio of a first, baseline level of ST2 and a second level of ST2 taken at a second time point, and a first level of an NP, e.g., NT-proBNP, taken at the second time point, to determine a first MACE risk score; and determining a second MACE risk score based upon a ratio of the first, baseline level of ST2 and a third ST2 level taken at a third time point, and a level of an NP, e.g., NT-proBNP, taken at the third time point, wherein the third time point is some time after the second time point, e.g., days, weeks, months, or years later. A comparison of the first and second MACE risk scores indicates whether the subject is declining, improving, or maintaining the same status, e.g., indicates the efficacy of the treatment in the subject. For example, a second MACE risk score that is lower than the first MACE risk score indicates that the treatment is effective.

As used herein, a "sample" includes any bodily fluid or tissue, e.g., one or more of blood, serum, plasma, urine, and body tissue. In certain embodiments, a sample is a serum, plasma, or blood sample.

An antibody that "binds specifically to" an antigen, binds preferentially to the antigen in a sample containing other proteins.

The methods and kits described herein have a number of advantages. For example, the methods can be used to determine whether a patient should be admitted or held as an inpatient for further assessment, regardless of whether a definitive diagnosis has been made. For example, the methods can be used for risk stratification of a given subject, e.g., to make decisions regarding the level of aggressiveness of treatment that is appropriate for the subject, based on their MACE risk score as determined by a method described herein. Better treatment decisions can lead to reduced morbidity and mortality, and better allocation of scarce health care resources. The methods described herein can be used to make general assessments as to whether a patient should be further tested to determine a specific diagnosis. The methods described herein can also be used for patient population risk stratification, e.g., to provide information about clinical performance or expected response to a therapeutic intervention. The methods described herein can be used regardless of the underlying cause or ultimate diagnosis, and therefore are not limited to specific indications.

Unless otherwise defined, all technical and scientific terms used herein have the same meaning as commonly understood by one of ordinary skill in the art to which this invention belongs. Methods and materials are described herein for use in the present invention; other, suitable methods and materials known in the art can also be used. The materials, methods, and examples are illustrative only and not intended to be limiting.

All publications, patent applications, patents, sequences, database entries, and other references mentioned herein are incorporated by reference in their entirety. In addition, the present application incorporates by reference the entire contents of U.S. patent application Ser. No. 11/789,169, and international patent application nos. PCT/US2007/067626, PCT/US2007/067914, and PCT/US2007/068024.

In case of conflict, the present specification, including definitions, will control.

Other features and advantages of the invention will be apparent from the following detailed description and Figures, and from the claims.

DETAILED DESCRIPTION

Figure 1:
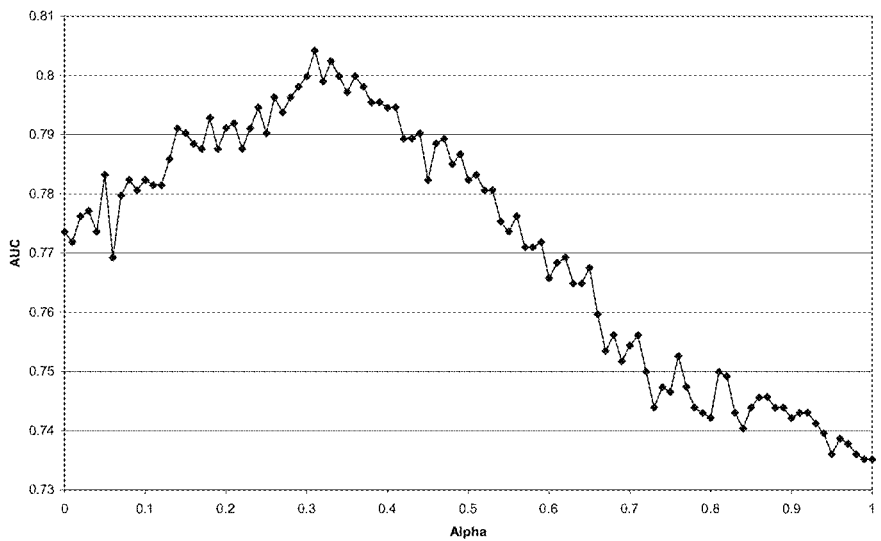
FIG. 1 is a line graph of Receiver Operating Characteristic (ROC) score analysis of the algorithm combining the ST2 ratio and the week 2 NT-proBNP value.

Clinical evaluation of patients, particularly patients with non-specific symptoms such as dyspnea or chest pain, is often challenging. The results described herein provide evidence that MACE risk scores based on ST2 and NT-proBNP are useful in the prognostic evaluation of patients, regardless of the underlying cause of their disease. The MACE risk score is a powerful indicator of severe disease and imminent death, as demonstrated herein in several different populations.

Predicting MACE

Elevated concentrations of ST2 are markedly prognostic for death within one year, with a dramatic divergence in survival curves for those with elevated ST2 soon after presentation, regardless of the underlying diagnosis. As one example, there is a dramatic relationship between elevations of ST2 and the risk for mortality within one year following presentation with dyspnea. The relationship between ST2 and death in dyspneic patients was independent of diagnosis, and superseded all other biomarker predictors of mortality in this setting, including other markers of inflammation, myo-necrosis, renal dysfunction, and most notably NT-proBNP, a marker recently described as having value for predicting death in this population (Januzzi et al., Arch. Intern. Med. 166(3):315-20 (2006)). Indeed, most of the mortality in the study was concentrated among subjects with elevated ST2 levels at presentation; however, the combination of an elevated ST2 and NT-proBNP was associated with the highest rates of death within one year.

Such a multi-marker approach for risk stratification has been generally proposed for patients with acute coronary syndromes (Sabatine et al., Circulation 105(15):1760-3 (2002)), but no such strategy has yet been proposed for the evaluation for the patient with non-specific symptoms such as undifferentiated dyspnea or general complaint of chest pain.

Determining Severity of Disease

Elevated MACE risk scores are correlated with the presence of severe disease in a subject, regardless of the underlying cause of the disease. As one example, in a population of patients presenting with chest pain, the highest scores were associated with an increased risk of adverse events, including transplantation, which are generally associated with the presence of severe disease.

Therefore, for undiagnosed subjects, the methods described herein can be used to determine how aggressively a diagnosis should be sought; a high ST2 level would indicate the presence of severe disease, and suggest that the subject should be treated as a high-risk case. For subjects with a known diagnosis, the methods described herein can be used to help determine the severity of the underlying pathology; again, a higher ST2 level is associated with more severe disease.

General Methodology—Determining a Subject's MACE Risk Score

In general, the methods described herein include evaluating circulating levels (e.g., levels in blood, serum, plasma, urine, or body tissue) of ST2 and NT-proBNP in a subject, e.g., a mammal, e.g., a human. These levels provide information regarding the subject's likelihood of experiencing an adverse outcome, e.g., mortality, e.g., within a specific time period, e.g., 30 days, 60 days, 90 days, 6 months, one year, two years, three years, or five years. These levels also provide information regarding the severity of disease in the subject. In some embodiments, a level of ST2 is determined a first time (T0), e.g., at presentation, e.g., at 2, 4, 6, 8, 12, 18, and/or 24 hours, and/or 1-3 or 1-7 days, after the onset of symptoms. Then levels of ST2 and NT-proBNP are determined a second time (T1); the second time point can be, e.g., at least 1, 2, 4, 6, 8, 12, 18, or 24 hours, 1-7 days, 1-14 days, or 2-14 days, e.g., up to 14 days, after the first time point. These levels are used to determine a MACE risk score, using the following formula:

$$X = (ST2\ T1/ST2\ T0) + \alpha \ln(NTproBNP\ T1)$$

The coefficient alpha is a weighting factor for the variable it acts on. In some embodiments, the coefficient alpha is between 0.25 and 0.5, e.g., about 3, e.g., 0.33.

Evaluating circulating levels of ST2 and NTpro-BNP in a subject typically includes obtaining a biological sample, e.g., serum, plasma or blood, from the subject. Levels of ST2 and NTpro-BNP in the sample can be determined by measuring levels of polypeptide in the sample, using methods known in the art and/or described herein, e.g., immunoassays such as enzyme-linked immunosorbent assays (ELISA). For example, in some embodiments a monoclonal antibody is contacted with the sample; binding of the antibody is then detected and optionally quantified, and levels of the protein are determined based on levels of antibody binding. Alternatively, levels of ST2 and NTpro-BNP mRNA can be measured, again using methods known in the art and/or described herein, e.g., by quantitative PCR or Northern blotting analysis.

In some embodiments, the MACE risk score is calculated using a computing device, e.g., a personal computer.

Once a MACE risk score has been determined, the MACE risk score can be compared to a reference score. In some embodiments, the reference score will represent a threshold level, above which the subject has an increased risk of death, and/or has a severe disease. The reference score chosen may depend on the methodology used to measure the levels of ST2. For example, in some embodiments, where circulating levels of soluble ST2 are determined using an immunoassay, e.g., as described herein, the reference score is about 3, e.g., 3.2 or 3.5, and a score above that reference level indicates that the subject has an increased risk of death, and/or has a severe disease.

Where more than one MACE risk score has been determined as described herein, a change in the score indicates whether the subject has an increased or decreased risk of death. A score that increases means that the subject has an increasing risk of imminent death, e.g., an increasingly poor prognosis, and that a treatment is not working or should be changed or initiated. Scores that decrease over time indicate that the subject has a decreasing risk of imminent death, e.g., an increasingly positive prognosis, and can be indicative of the efficacy of a treatment, for example, and the treatment should be continued, or, if the score becomes low enough, possibly discontinued. As one example, increasing scores may indicate a need for more aggressive treatment or hospitalization (e.g., initial admission or hospitalization in a more acute setting, e.g., in an intensive care unit, or the use of telemetry or other methods for monitoring the subject's cardiac status), while decreasing scores may indicate the possibility of less aggressive treatment, a short hospitalization, or discharge. This information allows a treating physician to make more accurate treatment decisions; for example, the subject may be admitted to the hospital as an inpatient, e.g., in an acute or critical care department Additional testing can be performed, e.g., to determine the subject's actual condition. More aggressive treatment may be administered either before or after additional testing. For example, in the case of a suspected myocardial infarction (MI), the subject may be sent for more extensive imaging studies and/or cardiac catheterization.

In some embodiments, the methods include the use of additional diagnostic methods to identify underlying pathology. Any diagnostic methods known in the art can be used, and one of skill in the art will be able to select diagnostic methods that are appropriate for the subject's symptoms. In some embodiments, the methods described herein include other diagnostic methods in addition to or as an alternative to the measurement of other biomarkers, e.g., physical measurements of lung function or cardiac function as are known in the art.

For example, the methods described herein include determining a MACE risk score along with measuring one or more additional biomarkers that aid in the subject's diagnosis. As one example, for a subject who has chest pain or dyspnea, biomarkers indicative of cardiac disease can be measured, e.g., cardiac troponin (cTn), e.g., cTnI, BNP, and/or ANP; alternatively or in addition, biomarkers of pulmonary disease can be measured, e.g., D-dimers for pulmonary embolism. Thus, in subjects presenting with symptoms that include MI in their differential diagnoses, the methods can include measuring levels of, e.g., cTnI, BNP, or proBNP in addition to determining a MACE risk score, to determine whether the subject is having an MI. In subjects presenting with symptoms that include heart failure (HF) in their differential diagnoses, the methods can include measuring levels of BNP or proBNP in addition to determining a MACE risk score, to determine whether the subject is having HF. In subjects presenting with symptoms that include COPD in their differential diagnoses, the methods can include measuring lung function in addition to determining a MACE risk score, to determine whether the subject has COPD. One of skill in the art will appreciate that there are a number of additional diagnostic methods that can be applied, depending on the situation and the subject's condition. In some embodiments, the methods include measuring levels of BUN, and the presence of elevated BUN and elevated determining a MACE risk score places the subject in the highest risk category.

ST2

The ST2 gene is a member of the interleukin-1 receptor family, whose protein product exists both as a trans-membrane form, as well as a soluble receptor that is detectable in serum (Kieser et al., FEBS Lett. 372 (2-3): 189-93 (1995); Kumar et al., J. Biol. Chem. 270(46):27905-13 (1995); Yanagisawa et al., FEBS Lett. 302(1):51-3 (1992); Kuroiwa et al., Hybridoma 19(2):151-9 (2000)). ST2 was recently described to be markedly up-regulated in an experimental model of heart failure (Weinberg et al., Circulation 106(23): 2961-6 (2002)), and preliminary results suggest that ST2 concentrations may be elevated in those with chronic severe HF (Weinberg et al., Circulation 107(5):721-6 (2003)) as well as in those with acute myocardial infarction (MI) (Shimpo et al., Circulation 109(18):2186-90 (2004)).

The trans-membrane form of ST2 is thought to play a role in modulating responses of T helper type 2 cells (Lohning et al., Proc. Natl. Acad. Sci. U.S.A 95(12):6930-5 (1998); Schmitz et al., Immunity 23(5):479-90 (2005)), and may play a role in development of tolerance in states of severe or chronic inflammation (Brint et al., Nat. Immunol. 5(4):373-9 (2004)), while the soluble form of ST2 is up-regulated in growth stimulated fibroblasts (Yanagisawa et al., 1992, supra). Experimental data suggest that the ST2 gene is markedly up-regulated in states of myocyte stretch (Weinberg et al., 2002, supra) in a manner analogous to the induction of the BNP gene (Bruneau et al., Cardiovasc. Res. 28(10):1519-25 (1994)).

Tominaga, FEBS Lett. 258:301-304 (1989), isolated murine genes that were specifically expressed by growth stimulation in BALB/c-3T3 cells; they termed one of these genes St2 (for Growth Stimulation-Expressed Gene 2). The St2 gene encodes two protein products: ST2, which is a soluble secreted form; and ST2L, a transmembrane receptor form that is very similar to the interleukin-1 receptors. The HUGO Nomenclature Committee designated the human homolog, the cloning of which was described in Tominaga et al., Biochim. Biophys. Acta. 1171:215-218 (1992), as Interleukin 1 Receptor-Like 1 (IL1RL1). The two terms are used interchangeably herein.

The mRNA sequence of the shorter, soluble isoform of human ST2 can be found at GenBank Acc. No. NM_003856.2, and the polypeptide sequence is at GenBank Acc. No. NP_003847.2; the mRNA sequence for the longer form of human ST2 is at GenBank Acc. No. NM_016232.4; the polypeptide sequence is at GenBank Acc. No. NP_057316.3. Additional information is available in the public databases at GeneID: 9173, MIM ID #601203, and UniGene No. Hs.66. In general, in the methods described herein, the soluble form of ST2 polypeptide is measured.

Methods for detecting and measuring ST2 are known in the art, e.g., as described in U.S. Pat. Pub. Nos. 2003/0124624, 2004/0048286 and 2005/0130136, the entire contents of which are incorporated herein by reference. Kits for measuring ST2 polypeptide are also commercially available, e.g., the ST2 ELISA Kit manufactured by Medical & Biological Laboratories Co., Ltd. (MBL International Corp., Woburn, Mass.), no. 7638. In addition, devices for measuring ST2 and other biomarkers are described in U.S. Pat. Pub. No. 2005/0250156.

Natriuretic Peptides

Natriuretic peptides are a family of vasoactive peptide hormones that act as balanced arterial and venous vasodilators, regulating natriuresis and diuresis. Circulating levels of these hormones are under investigation for use in enhancing diagnostic and prognostic assessment of patients with cardiovascular disease. Previous studies have demonstrated that circulating levels of NT-proBNP are increased in patients with acute MI and predict mortality (Talwar et al., Eur. Heart J. 21:1514-1521 (2000); Omland et al., Am. J. Cardiol. 76:230-235 (1995) Sabatine et al., J. Am. Coll. Cardiol. 44:1988-1995 (2004), demonstrated a link between the severity of an acute ischemic insult and the circulating levels of BNP. Methods for measuring NT-proBNP are known in the art, see, e.g., Talwar et al., 2000, supra; Omland et al., 1995, supra; Sabatine et al., 2004, supra; Alehagen and Dahlström, "Can NT-proBNP predict risk of cardiovascular mortality within 10 years? Results from an epidemiological study of elderly patients with symptoms of heart failure," Int J Cardiol. 2008 Apr. 11 [Epub ahead of print]; and Kaysak et al., Clin Chem. 54(4):747-51 (2008).

It is believed that, while the examples presented herein relate to NT-proBNP, any of the NPs can be used in the methods described herein. In some embodiments, more that one NP can be measured.

Other Biomarkers

The methods described herein can also include measuring levels of other biomarkers in addition to ST2 and an NP. Suitable biomarkers include troponin, CRP, IL-6, D-dimers, BUN, liver function enzymes, albumin, measures of renal function, e.g., creatinine, creatinine clearance rate, or glomerular filtration rate, and/or bacterial endotoxin. Methods for measuring these biomarkers are known in the art, see, e.g., U.S. Pat. Pub. Nos. 2004/0048286 and 2005/0130136 to Lee et al.; Dhalla et al., Mol. Cell. Biochem. 87:85-92 (1989); Moe et al., Am. Heart. J. 139:587-95 (2000); Januzzi et al., Eur. Heart J. 27(3):330-7 (2006); Maisel et al., J. Am. Coll. Cardiol. 44(6):1328-33 (2004); and Maisel et al., N. Engl. J. Med. 347(3):161-7 (2002), the entire contents of which are incorporated herein by reference. Liver function enzymes include alanine transaminase (ALT); aspartate transaminase (AST); alkaline phosphatase (ALP); and total bilirubin (TBIL).

In these embodiments, a MACE risk score and levels of one or more additional biomarkers are determined, and the information from the score and a comparison of the biomarkers with their respective reference levels provides additional information regarding the subject's risk of death and/or the presence of a severe disease in the subject, which may provide more accurate and specific information regarding the subject's risk. The levels can then be compared to a reference ratio that represents a threshold ratio above which the subject has an increased risk of death, and/or has a severe disease.

Selecting a Treatment—Aggressive vs. Conservative

Once it has been determined that a subject has a MACE risk score above a predetermined reference score, the information can be used in a variety of ways. For example, if the subject has an elevated score, e.g., as compared to a reference level, a decision to treat aggressively can be made, and the subject can be, e.g., admitted to a hospital for treatment as an inpatient, e.g., in an acute or critical care department. Portable test kits could allow emergency medical personnel to evaluate a subject in the field, to determine whether they should be transported to the ED. Triage decisions, e.g., in an ED or other clinical setting, can also be made based on information provided by a method described herein. Those patients with high scores can be prioritized over those with lower scores.

The methods described herein also provide information regarding whether a subject is improving, e.g., responding to a treatment, e.g., whether a hospitalized subject has improved sufficiently to be discharged and followed on an outpatient basis. In general, these methods will include d determining a MACE risk score for the subject multiple times. A decrease in MACE risk score over time indicates that the subject is likely to be improving. The most recent MACE risk score can also be compared to a reference score, as described herein, to determine whether the subject has improved sufficiently to be discharged.

The subject may also be considered for inclusion in a clinical trial, e.g., of a treatment that carries a relatively high risk. The subject can be treated with a regimen that carries a relatively higher risk than would be considered appropriate for someone who had a lower risk of imminent MACE, e.g., a MACE within 30 days or within 1 year of presentation.

Beyond the clinical setting, information regarding a subject's MACE risk score can be used in other ways, e.g., for payment decisions by third party payors, or for setting medical or life insurance premiums by insurance providers. For example, a high MACE risk score, e.g., a score above a predetermined threshold score, may be used to decide to increase insurance premiums for the subject.

Patient Populations

The methods described herein are useful in a wide variety of clinical contexts. For example, the methods can be used for general population screening, including screening by doctors, e.g., in hospitals and outpatient clinics, as well as the ED. As one example, a MACE risk score can be determined at any time, and if the MACE risk score is elevated, the physician can act appropriately.

Although the methods described herein can be used for any subject, at any time, they are particularly useful for those subjects for whom a diagnosis, or the severity of a condition, is difficult to determine. For example, such subjects may present with non-specific symptoms, e.g., symptoms that do not indicate a specific diagnosis. Non-specific symptoms include, but are not limited to, chest pain or discomfort, shortness of breath, nausea, vomiting, eructation, sweating, palpitations, lightheadedness, fatigue, and fainting. Each symptom can have varied etiology.

Chest Pain

Chest pain is the chief complaint in about 1 to 2 percent of outpatient visits, and although the cause is often noncardiac, heart disease remains the leading cause of death in the United States. Therefore, distinguishing between serious and benign causes of chest pain is crucial. The methods described herein are useful in making this determination.

A subject presenting to the ED with chest pain may have esophageal pain, an ulcer, acute lung problems such as pulmonary embolus (PE) (potentially fatal), rupturing or dissecting aneurysm (highly lethal), gall bladder attack, pericarditis (inflammation of the sack around the heart), angina pectoris (cardiac pain without damage), or an MI (potentially fatal). A precise diagnosis may be difficult to make immediately, but the decision whether to admit the subject or to treat them conservatively should generally be made immediately. If the methods described herein indicate that the subject has an increased risk of an adverse clinical outcome, e.g., imminent MACE or severe disease, then the decision can be made to treat the subject aggressively, to potentially prevent the adverse outcome.

Additional information about treatment and diagnosis of chest pain may be found, e.g., in Cayley, Am. Fam. Phys. 72(10):2012-2028 (2005).

Dyspnea

Dyspnea, or shortness of breath (also defined as abnormal or uncomfortable breathing), is a common symptom of subjects on presentation to the ED. The differential diagnosis for dyspnea includes four general categories: (1) cardiac, (2) pulmonary, (3) mixed cardiac or pulmonary, and (4) noncardiac or nonpulmonary.

Cardiac causes of dyspnea include right, left, or biventricular congestive heart failure with resultant systolic dysfunction, coronary artery disease, recent or remote myocardial infarction, cardiomyopathy, valvular dysfunction, left ventricular hypertrophy with resultant diastolic dysfunction, asymmetric septal hypertrophy, pericarditis, and arrhythmias.

Pulmonary causes include obstructive (e.g., chronic obstructive pulmonary disease (COPD) and asthma) and restrictive processes (e.g., extrapulmonary causes such as obesity, spine or chest wall deformities, and intrinsic pulmonary pathology such as interstitial fibrosis, pneumoconiosis, granulomatous disease or collagen vascular disease).

Mixed cardiac and pulmonary disorders include COPD with pulmonary hypertension and cor pulmonale, deconditioning, pulmonary emboli, and trauma.

Noncardiac or nonpulmonary disorders include metabolic conditions such as anemia, diabetic ketoacidosis and other, less common causes of metabolic acidosis, pain in the chest wall or elsewhere in the body, and neuromuscular disorders such as multiple sclerosis and muscular dystrophy. Obstructive rhinolaryngeal problems include nasal obstruction due to polyps or septal deviation, enlarged tonsils, and supraglottic or subglottic airway stricture.

Dyspnea can also present as a somatic manifestation of psychiatric disorders, e.g., an anxiety disorder, with resultant hyperventilation.

Additional information regarding the evaluation and treatment of dyspnea can be found, e.g., in Morgan and Hodge, Am. Fam. Phys. 57(4):711-718 (1998).

Special Populations

Certain populations of subjects may benefit particularly from the methods described herein. These subjects include people for whom BNP or NT-proBNP alone is less useful, such as in those with impaired renal function (Anwaruddin et al., J. Am. Coll. Cardiol. 47(1):91-7 (2006); McCullough et al., Am. J. Kidney Dis. 41(3):571-9 (2003)), or in those who are overweight (Body Mass Index (BMI) of 25-29) or obese (BMI≥30) (Krauser et al., Am. Heart J. 149(4):744-50 (2005); McCord et al., Arch. Intern. Med. 164(20):2247-52 (2004)). It is known and accepted in the field that patients with a high BMI usually have levels of natriuretic peptide that are lower than expected relative to a normal body mass patient for the same level of disease; the exact mechanism for this phenomenon is not known. It has been shown that circulating levels of ST2 are not influenced by BMI, therefore, the determination of a MACE risk score is more useful than natriuretic peptide levels alone in subjects with high BMI. Thus, the methods described herein can include determining a subject's BMI, and if the subject is overweight or obese, selecting the patient for determination of a MACE risk score, as described herein.

EXAMPLES

The invention is further described in the following examples, which do not limit the scope of the invention described in the claims.

Example 1. Derivation of a Formula Combining ST2 with NT-proBNP for MACE Risk Determination in Patients with Acute Decompensated Heart Failure (HF)

Measurement of either ST2 or NT-proBNP at presentation or at time points during treatment or follow-up have been individually shown to be valuable for prognosis. It has also been determined that the strongest measurement for prognosis is the change in ST2 between two time points. In this analysis forty-eight (48) patients with established symptomatic HF attending two HF clinics with signs and symptoms of worsening HF were evaluated. Baseline (T0) and week 2 (T1) measurements of sST2 and amino-terminal pro-B type natriuretic peptide (NT-proBNP) concentrations were obtained. Adverse cardiac events (death, admission for HF, and heart transplant) were reported in 56% of patients during the 1 year follow-up period. The area under the ROC curve (AUC) values shown in Table 1 calculated for a series of measurements made in this data set illustrate this point when using all cardiac events as the outcome.

TABLE 1

Summary of ROC AUC values for each individual measurement and ratio values for events within 1 year

|  | AUC | SE | 95% CI |
| --- | --- | --- | --- |
| ST2_T0 | 0.622 | 0.082 | 0.470 to 0.757 |
| ST2_T1 | 0.583 | 0.0827 | 0.432 to 0.724 |
| NTproBNP_T0 | 0.479 | 0.0845 | 0.333 to 0.628 |
| NTproBNP_T1 | 0.619 | 0.081 | 0.467 to 0.755 |
| ST2_R | 0.772 | 0.0675 | 0.628 to 0.880 |
| NTproBNP_R | 0.717 | 0.0737 | 0.568 to 0.837 |

Using the ST2 ratio in a simple binary stratification approach we get the results shown in Table 2, in this case using the ROC optimal threshold value of 0.75.

TABLE 2

Summary of patient stratification for risk of cardiac events within 1 year using an ST2 ratio threshold of 0.75

|  | ST2 Ratio | | median | mean |
| --- | --- | --- | --- | --- |
|  | <0.75 | ≥0.75 | 0.875 | 1.030 |
| N | 19 | 29 |  |  |
| N Event | 6 | 20 |  |  |
| % Event | 31.6% | 69.0% |  |  |
| PPV | 69% |  |  |  |
| NPV | 68% |  |  |  |
| RR | 2.2 |  |  |  |

As can be seen in this Table the ROC optimal threshold is lower than either the median or the mean. However if a higher threshold, such as the median value is used, the relative risk decreases to 1.9 so for the purpose of this analysis the threshold of 0.75, which provides the highest prognostic accuracy, will be used.

In other studies (Januzzi et al., J. Am. Coll. Cardiol. 50:607-613 (2007); Mueller et al., Clin. Chim. 54(4):752-756 (2008)) it has also been observed that there is a synergistic relationship between ST2 and NT-proBNP when used for risk stratification or prognosis. In an effort to both confirm that relationship in this cohort and to identify the most powerful method for using ST2 and NT-proBNP together various mathematical combinations were considered. Table 3 represents the best results obtained in a simple binary analysis where the change in ST2 represented as a ratio is combined with the NT-proBNP value at the second time point. The threshold of 0.75 for the ST2 ratio value was determined by ROC analysis, and verified subjectively, to be optimal and an NT-proBNP value of 1000 pg/ml is generally considered ideal for prognosis within a 1 year followup period.

TABLE 3

Summary of patient stratification using the ST2 Ratio and the week 2 NT-proBNP value, using thresholds of 0.75 for the ST2 ratio and 1000 pg/ml for NT-proBNP

| | ST2 R & NTproBNP W2 | | | | | |
|---|---|---|---|---|---|---|
| 0.75, 1000 | ST2−, NT− | ST2−, NT+ | ST2+, NT− | ST2+, NT+ | both− | either+ |
| N | 4 | 15 | 4 | 25 | 4 | 44 |
| N Event | 0 | 6 | 2 | 18 | 0 | 26 |
| % Event | 0.0% | 40.0% | 50.0% | 72.0% | 0.0% | 59.1% |

Although effective at identifying both the highest risk and lowest risk patients, the weakness in this approach is that there is a very small number of patients in the lowest risk group and a large percentage of patients in the indeterminate range.

To better define the functional utility of the ST2 ratio combined with an NT-proBNP value a formula was developed:

$$X = (ST2\ T1/ST2\ T0) + \alpha\ \ln(NTproBNP\ T1)$$

This formula was developed by evaluating the result as a function of ROC AUC for a range of coefficients associated with the NT-proBNP term. The result from this series of calculations is shown in FIG. 1.

The maximum AUC value was achieved at a coefficient for a of 0.33 resulting in the final equation being:

$$X = (ST2\ T1/ST2\ T0) + 0.33\ \ln(NTproBNP\ T1)$$

Figure 2:
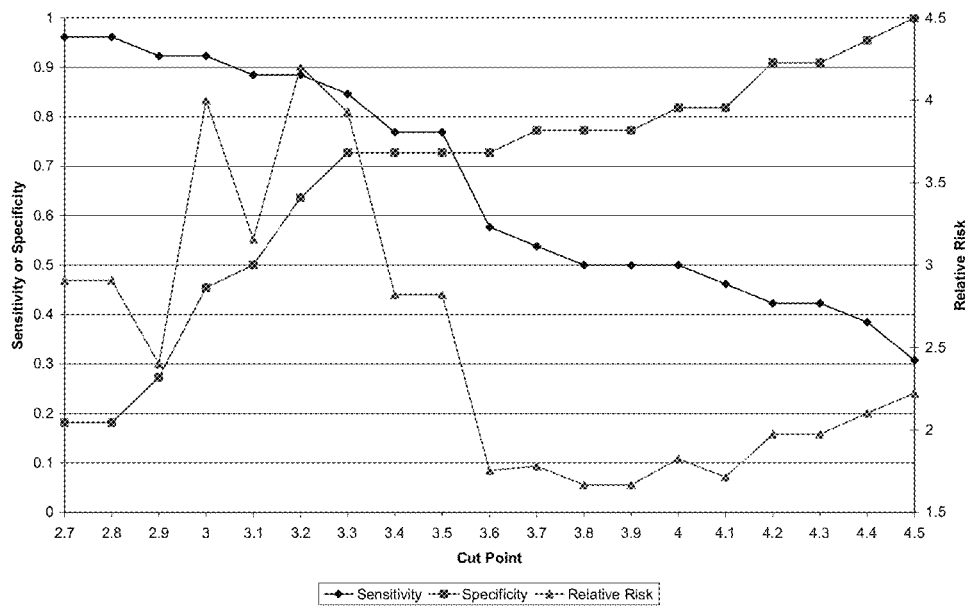
FIG. 2 is a line graph of sensitivity, specificity and relative risk plotted as a function of the score.

Using this algorithm in a series of calculations comparing the sensitivity, specificity and relative risk (right side axis) we get the plot in FIG. 2.

Figure 3:
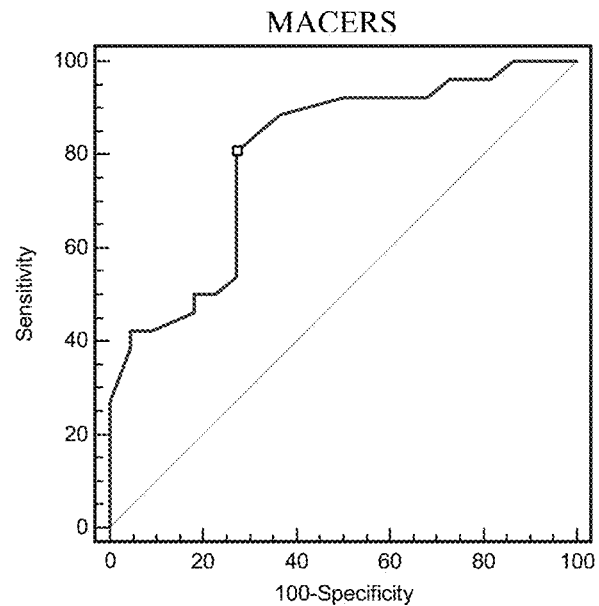
FIG. 3 is a ROC curve for MACE risk score and events within 1 year.

In this plot the score value resulting in the maximum relative risk value is 3.2. ROC analysis of this data confirms that the optimal threshold value is 3.3, illustrated in FIG. 3. Also note that the AUC value using this score is 0.80 as compared to 0.77 for the ST2 ratio and 0.72 for the NT-proBNP ratio, which generated the next highest AUC values.

When this score is used, at the threshold value of 3.2, to stratify patients in this cohort who are at risk of events; admission, transplant or mortality, a clear distinction between low risk and high risk patients is achieved. These results are illustrated in Table 4.

TABLE 4

Summary of patient stratification for risk of adverse events within 1 year using a score cutpoint of 3.2

| | Score | | median | mean |
|---|---|---|---|---|
| | <3.2 | ≥3.2 | 3.55 | 3.71 |
| N | 17 | 31 | | |
| N Event | 3 | 23 | | |

TABLE 4-continued

Summary of patient stratification for risk of adverse events within 1 year using a score cutpoint of 3.2

| | Score | | median | mean |
|---|---|---|---|---|
| % Event | 17.6% | 74.2% | | |
| PPV | 74.2% | | | |
| NPV | 82.4% | | | |
| RR | 4.2 | | | |

Directly comparing these results with the results using the ST2 ratio alone, shown in Table 2, illustrates that by combining the ST2 ratio with an NT-proBNP value all of the relevant parameters representing assessment of risk prediction are stronger; PPV, NPV and RR.

For comparison the stratification results for the next strongest value, the NT-proBNP ratio is summarized in Table 5. The values using the NT-proBNP ratio are much lower than when the ST2 ratio is used or from the formula combining ST2 with NT-proBNP.

TABLE 5

Summary of patient stratification for risk of adverse events within 1 year using the NT-proBNP ratio

| | NT-proBNP Ratio | | median | mean |
|---|---|---|---|---|
| | <0.75 | ≥0.75 | 0.74 | 0.83 |
| N | 24 | 24 | | |
| N Event | 10 | 16 | | |
| % Event | 41.7% | 66.7% | | |
| PPV | 66.7% | | | |
| NPV | 58.3% | | | |
| RR | 1.1 | | | |

TABLE 6

Comparison of ST2 Ratio and Score Values

| | NTproBNP Ratio | ST2 Ratio | Score |
|---|---|---|---|
| PPV | 67% | 69% | 74% |
| NPV | 58% | 68% | 82% |
| RR | 1.1 | 2.2 | 4.2 |

Figure 4A:
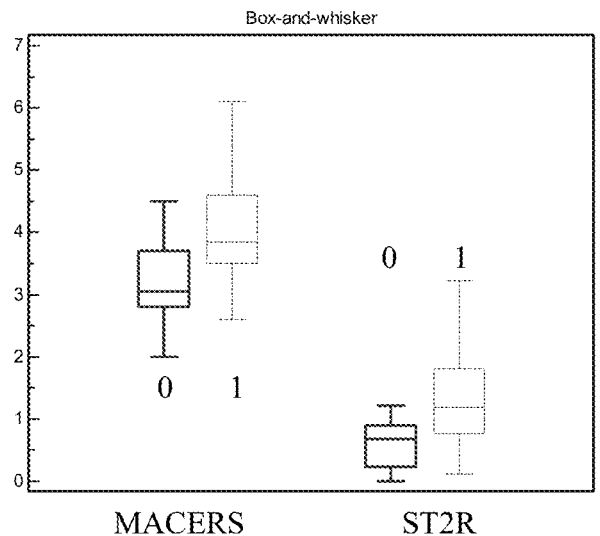
FIG. 4A is a whisker box plot of MACE risk score and ST2 ratio for cardiac events within 1 year.

The relative differences between the score and ST2 ratio values can also be represented graphically using whisker box plots, as shown in FIG. 4A. As expected, both groups had statistically significant resolution between the event and no event clusters, P=0.0004 for Score and P=0.0013 for ST2 ratio.

Figure 4B:
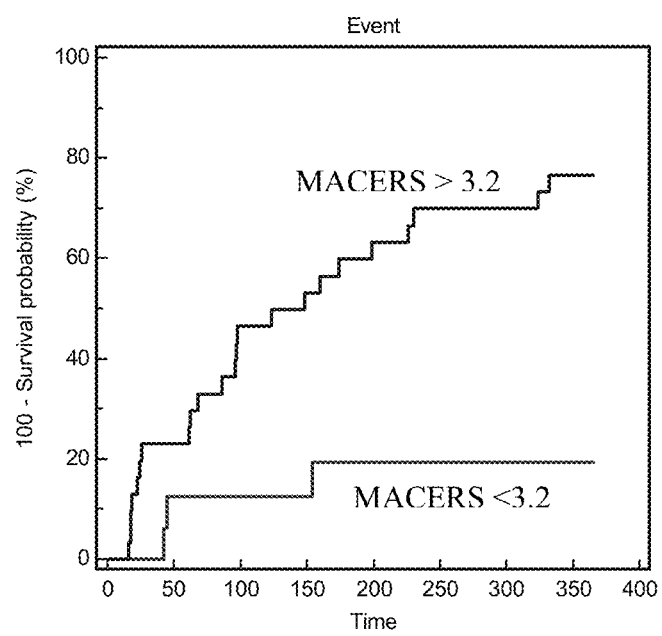
FIG. 4B is a Kaplan-Meier Survival Curve for events using MACE risk score at a threshold of 3.2.
Figure 5:
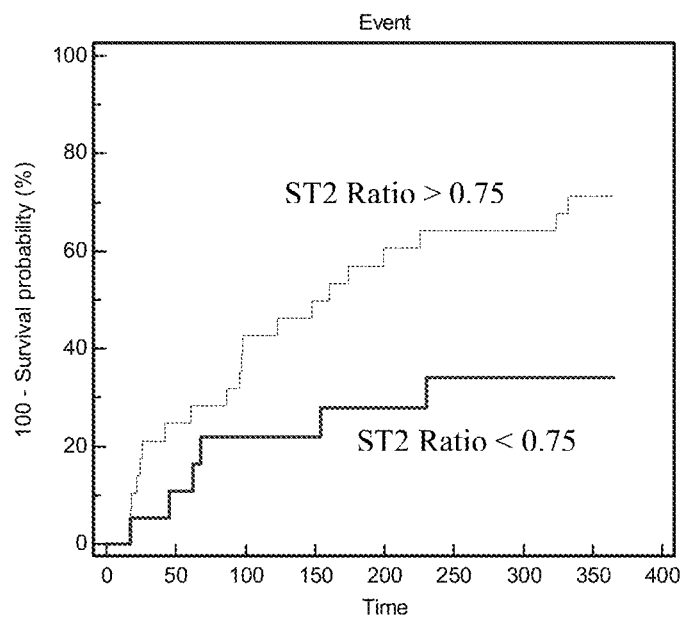
FIG. 5 is a Kaplan-Meier Survival Curve for events using the ST2 ratio.
Figure 6:
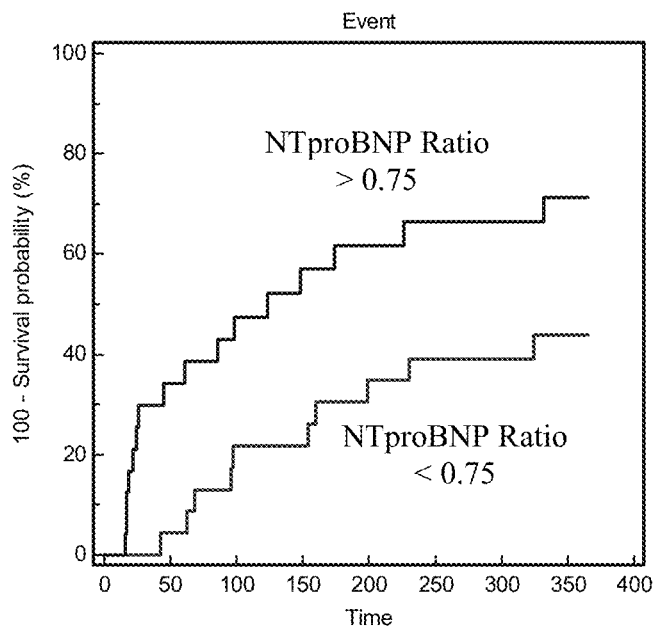
FIG. 6 is a Kaplan-Meier Survival Curve for events using NT-proBNP ratio at a threshold of 0.75.
Figure 7:
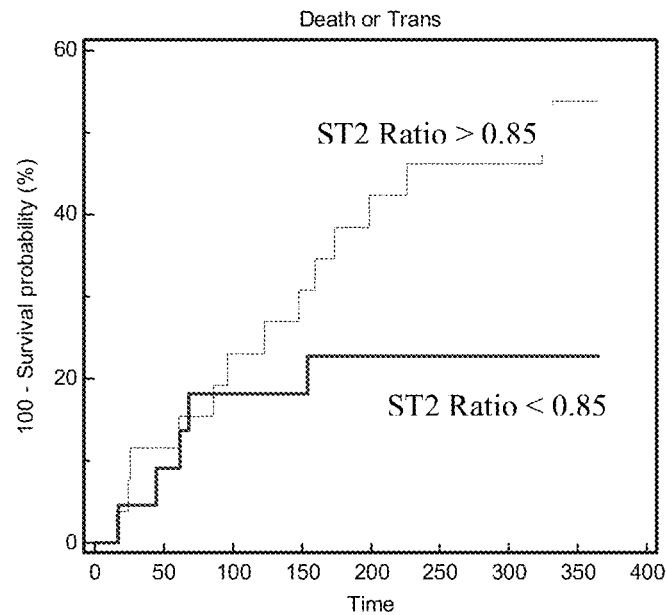
FIG. 7 is a Kaplan-Meier Survival Curve for death or transplant within 1 year using ST2 ratio at a threshold of 0.85.
Figure 8:
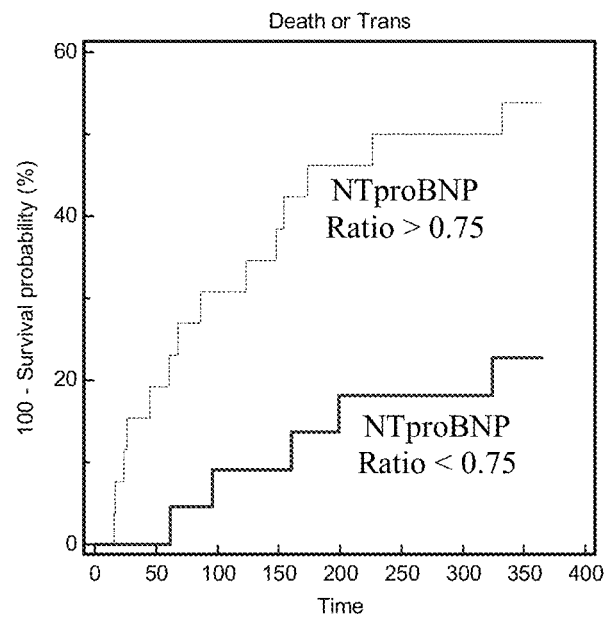
FIG. 8 is a Kaplan-Meier Survival Curve for death or transplant within 1 year using NT-proBNP ratio at a threshold of 0.70.

The distinction between the score generated from this formula and the ratio for ST2 values is also observed when analyzed by Kaplan-Meier survival curves. FIG. 4B shows the survival curve results for the formula score with a calculated hazard ratio of 5.93. Consistent with the previous calculations, FIG. 5 shows that this same analysis for the ST2 ratio had a hazard ratio of 2.72, which is similar to the value calculated for the NT-proBNP ratio of 2.39, as shown in FIG. 6.

The hazard ratios calculated from the Kaplan-Meier curves was consistent with the Cox proportional-hazards regression analysis. Table 7 summarizes the hazard ratio (HR) values from both calculations for the three most informative measurements.

TABLE 7

Summary of hazard ratio values for risk of event at 1 year followup

|  | CCD Score | | ST2 ratio | | NT-proBNP ratio | |
| --- | --- | --- | --- | --- | --- | --- |
|  | HR | p | HR | p | HR | p |
| K-M curve | 5.93 | 0.0009 | 2.72 | 0.025 | 2.39 | 0.025 |
| cox | 6.07 | 0.003 | 2.73 | 0.03 | 2.12 | 0.059 |

This formula was also evaluated for accuracy in predicting the more definitive endpoints of death and/or transplant, as shown in Table 8.

TABLE 8

Summary of ROC AUC values for each individual measurement and ratio values for death or transplant within 1 year

|  | AUC | SE | 95% CI |
| --- | --- | --- | --- |
| ST2_S0 | 0.625 | 0.0813 | 0.474 to 0.761 |
| ST2_S2 | 0.521 | 0.0858 | 0.372 to 0.667 |
| NTPROBNP_S0 | 0.564 | 0.086 | 0.414 to 0.707 |
| NTPROBNPS2 | 0.679 | 0.0813 | 0.528 to 0.806 |
| ST2_R | 0.706 | 0.0793 | 0.557 to 0.828 |
| NTPROBNP_R | 0.672 | 0.0818 | 0.521 to 0.800 |

In this analysis, the only variable that had an AUC greater than 0.7 is the ST2 ratio. For the outcome of death or transplant a threshold value of 0.85 for the ST2 ratio was determined by ROC analysis to be optimal, as shown in Table 9.

TABLE 9

ST2 Ratio ROC Values

| Criterion | Sensitivity | 95% CI | Specificity | 95% CI | +LR | −LR |
| --- | --- | --- | --- | --- | --- | --- |
| >0.85 | 68.42 | 43.5-87.3 | 58.62 | 38.9-76.5 | 1.65 | 0.54 |

When these results were compared to a generally accepted threshold value for a change in NT-proBNP of 0.7 (the ROC optimal value for the NT-proBNP ratio is 0.58), the results shown in Table 10 were generated. Note that the optimal threshold value for the ST2 ratio and risk of death or transplant within 1 year was higher at 0.85 than the optimal threshold value of 0.75 for any adverse cardiac event within 1 year.

TABLE 10

Summary of patient stratification for risk of death or transplant within 1 year comparing the ST2 ratio and the NT-proBNP ratio

|  | ST2 Ratio | | NT-proBNP Ratio | |
| --- | --- | --- | --- | --- |
|  | <0.85 | ≥0.85 | <0.7 | ≥0.7 |
| N | 22 | 26 | 22 | 26 |
| N Event | 5 | 14 | 5 | 14 |
| % Event | 22.7% | 53.8% | 23% | 54% |
| PPV |  | 53.8% |  | 53.8% |
| NPV | 77.3% |  | 77.3% |  |
| RR |  | 2.4 |  | 2.4 |

Although each biomarker had similar predictive strength, of the five patients identified below the threshold, only one was predicted by both biomarkers.

Kaplan-Meier survival curve analysis also showed that, when considered individually in this population, the ST2 ratio and the NT-proBNP ratio were functionally indistinguishable in regards to outcome prediction, although the curve for the NT-proBNP ratio diverges early and remains divergent, whereas the curve for the ST2 ratio diverges much later. For the ST2 ratio the HR is 2.66 (p=0.0506), while for the NT-proBNP ratio the HR is 2.60 (P=0.0201).

The results obtained by Cox proportional-hazards regression analysis are slightly different. When analyzed individually the HR values were 1.94 for the ST2 ratio and 0.55 for the NT-proBNP ratio, and were almost the same when analyzed together at 2.03 for the ST2 ratio and 0.53 for the NT-proBNP ratio. The p value was not significant for either variable, at 0.176 and 0.168 respectively.

Figure 9:
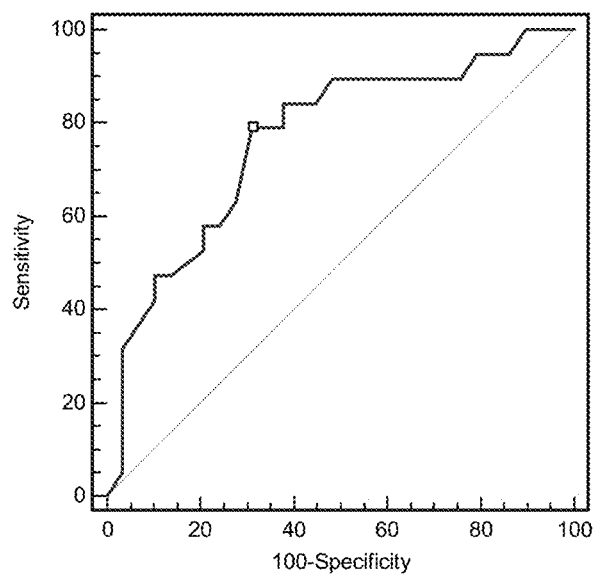
FIG. 9 is a ROC curve for Score and death or transplant within 1 year. Although ROC analysis identifies 3.5 as the optimal threshold, additional analysis confirms that the previously identified threshold of 3.2 provides better prognostic accuracy.

However, as was observed when events were evaluated as the outcome parameter, if the ST2 ratio was combined with the second NT-proBNP value the results of ROC analysis illustrate greater predictive accuracy using this formula, as shown in FIG. 9.

Figure 10:
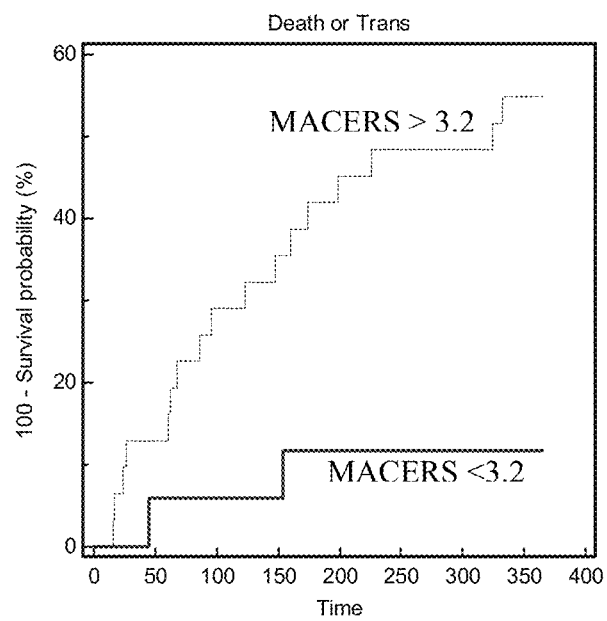
FIG. 10 is a Kaplan-Meier Survival Curve for death or transplant within 1 year using the MACE risk score at the threshold of 3.2.

Although ROC analysis identified 3.5 as the optimal threshold, additional analysis confirms that the previously identified threshold of 3.2 provides better prognostic accuracy. The HR from Kaplan-Meier survival analysis (FIG. 10) was 6.02 (p=0.0060). The HR calculated from the Cox proportional-hazards regression analysis was very similar at 6.08 (p=0.016).

Table 11 provides a summary of relative risk calculations comparing the values previously determined for the ST2 and NT-proBNP ratios as well as the MACE risk score.

TABLE 11

Summary of patient stratification for risk of death or transplant within 1 year
Death or Transplant within 1 Year

|  | ST2 Ratio | | NT-proBNP Ratio | | MACE risk score | |
| --- | --- | --- | --- | --- | --- | --- |
|  | <0.85 | ≥0.85 | <0.7 | ≥0.7 | <3.2 | ≥3.2 |
| N | 22 | 26 | 22 | 26 | 17 | 31 |
| N Event | 5 | 14 | 5 | 14 | 2 | 17 |
| % Event | 22.7% | 53.8% | 23% | 54% | 11.8% | 54.8% |
| PPV |  | 53.8% |  | 53.8% |  | 54.8% |
| NPV | 77.3% |  | 77.3% |  | 88.2% |  |
| RR |  | 2.4 |  | 2.4 |  | 4.7 |

Figure 11:
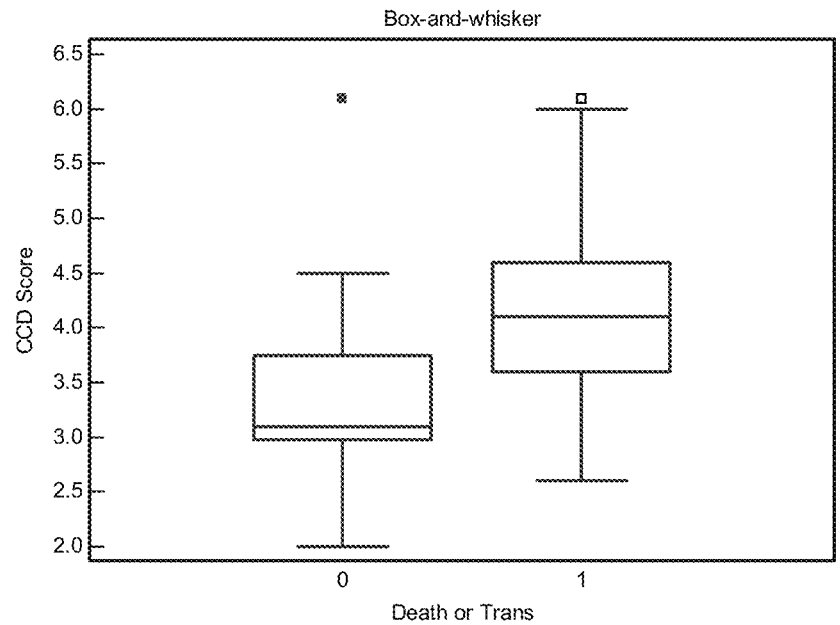
FIG. 11 is a whisker box plot showing MACE risk score for events or no-events (death or transplant).
Figure 12:
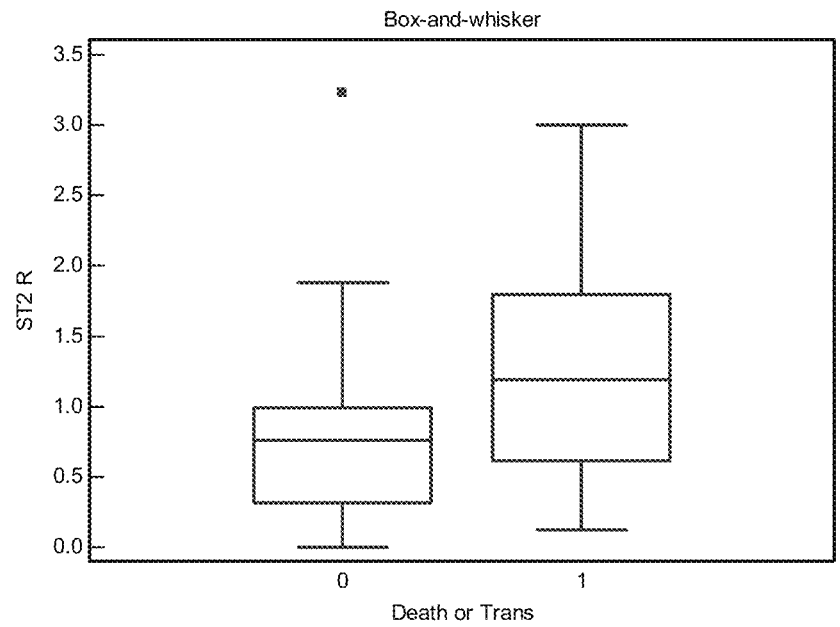
FIG. 12 is a whisker box plot showing ST2 ratio for events or no-events (death or transplant).
Figure 13:
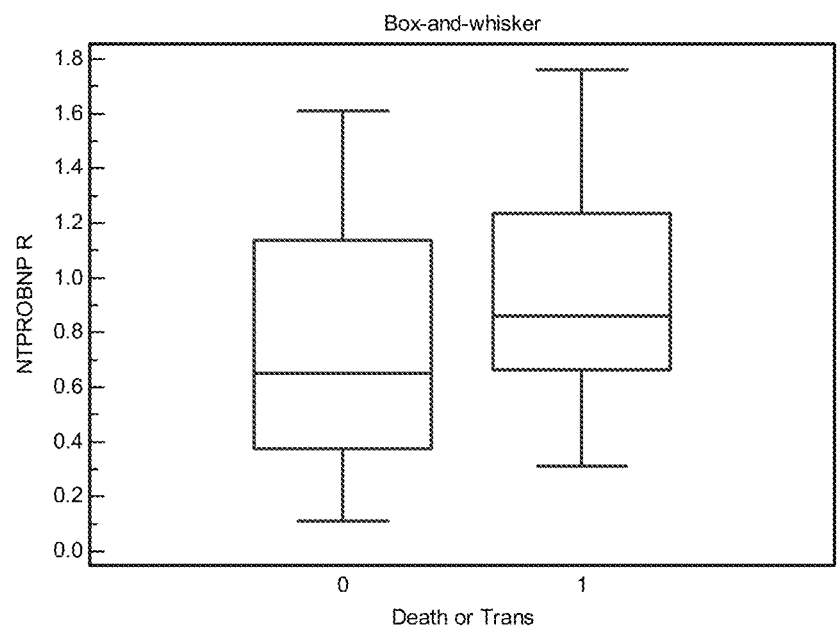
FIG. 13 is a whisker box plot showing NT-proBNP ratio for events or no-events (death or transplant).

A simple box plot (FIG. 11) illustration confirms the distinction between the event and non-event group for the MACE risk score values. For this plot p=0.002. Note that the median values do not overlap with the 25-75% boundary. This same comparison for the ST2 ratio and the NT-proBNP ratio is shown in FIGS. 12 and 13. The p values for these plots are 0.017 and 0.046 respectively and the distinction between the event and no-event group is not as definitive as it is for the MACE risk score.

Conclusion

As derived from this data set, the described formula combining the ratio of ST2 values between two time points and an NT-proBNP value measured at the second time point provides the strongest and most accurate measure of risk that a patient will experience an adverse cardiac event defined as admission, transplant or death.

Example 2. Validation Analysis of the Formula Combining ST2 with NT-proBNP for MACE Risk Prediction In the study described in this example, 150 patients hospitalized with acutely destabilized HF were followed at the Veteran Affairs Healthcare System in San Diego, Calif. Multiple cardiac-related parameters were measured, including ST2, BNP, NT-proBNP, and blood urea nitrogen (BUN). Plasma samples were collected at six time points between admission and discharge. Biomarker concentrations were correlated to survival at 90 days. These 150 patients were sorted further by the following criteria to optimize coordination between the various measurements that were made and the times that these measurements were made:

1. ST2 value on day 1
2. ST2 value on day 3 or later for a minimum elapsed time of 2 days
3. NT-proBNP value on the same last day as the last ST2 value
4. Alive at discharge This sort resulted in a total remaining N of 107 patients, with 35 events, readmission or death, within 90 days and 13 of those events were deaths within 90 days. The following analysis compares the various individual measurements for accuracy in predicting mortality within 90 days and validates the formula combining ST2 with NT-proBNP.

Figure 14:
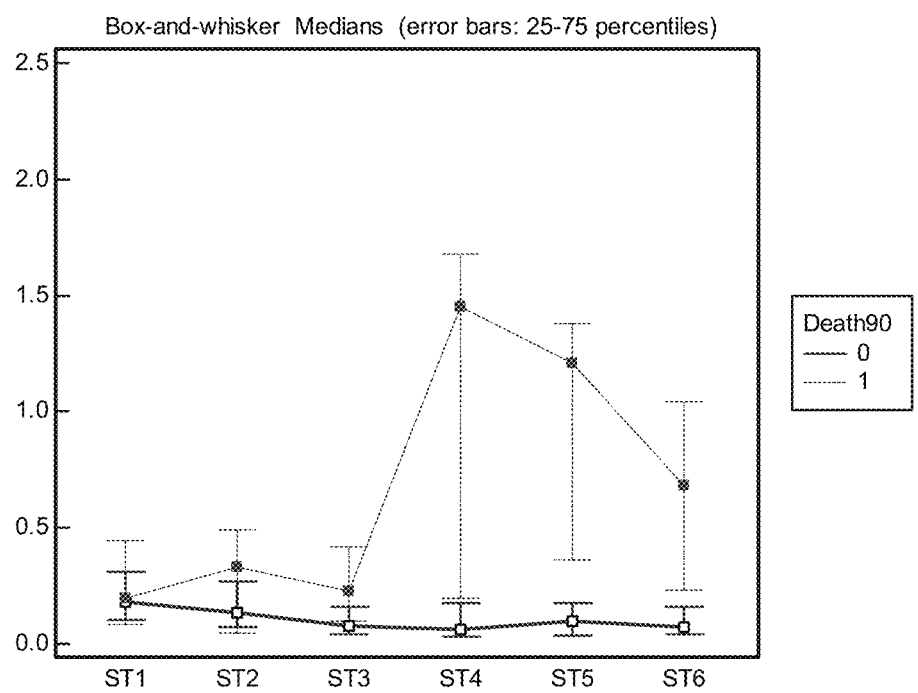
FIG. 14 is a whisker and dot plot showing ST2 values by days.
Figure 15:
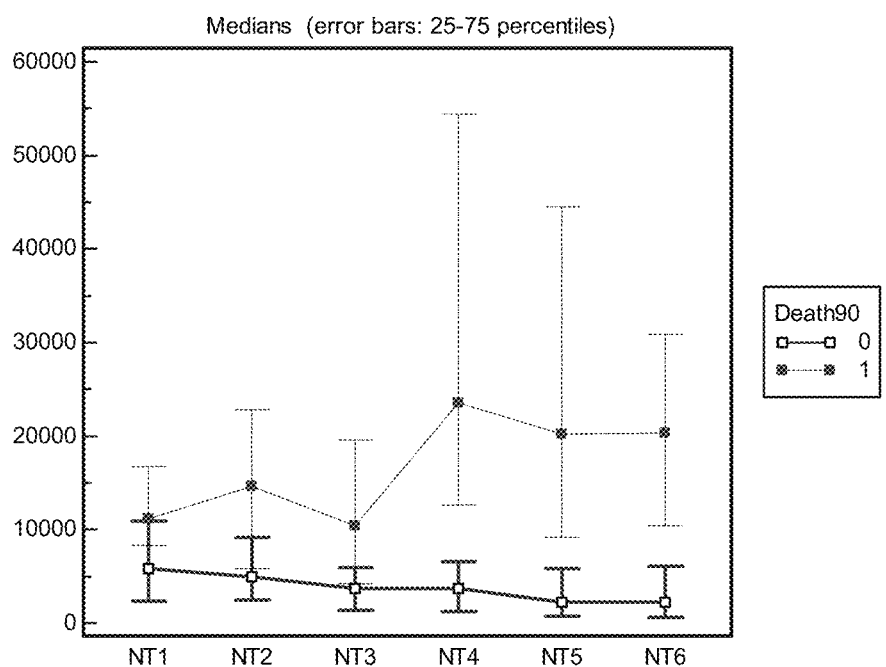
FIG. 15 is a whisker and dot plot showing NT-proBNP values by day.
Figure 16:
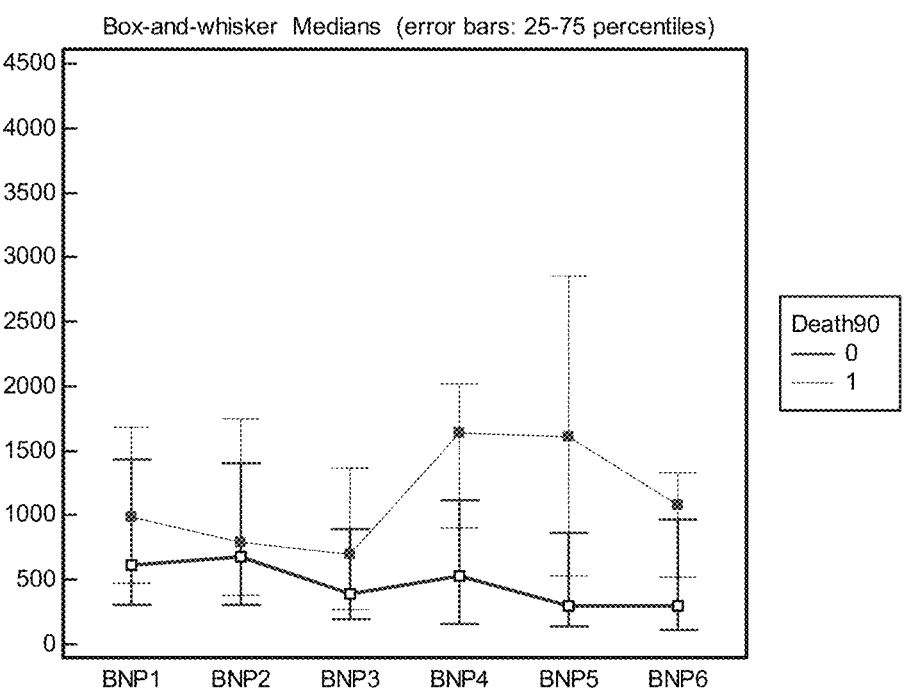
FIG. 16 is a whisker and dot plot showing BNP values by day.

If the biomarkers are reported by day and as a function of whether the patient survived or died there is a clear distinction over time. In patients who did not survive the values for ST2, as well as BNP and NT-proBNP increased, whereas in those patients who did survive these values decreased and remained low. In FIGS. 14-16, the median is plotted with error bars representing the $25^{th}$-$75^{th}$ percentiles.

In this analysis, by day four (three elapsed days), all three biomarkers achieved maximum separation in median values between survivors and decedents, but only ST2 and NT-proBNP were also able to achieve and maintain significant resolution not only between the median values but also between the $25^{th}$-$75^{th}$ percentile values.

ROC analysis, summarized in Table 13, affirmed this observation with maximum AUC values for each biomarker at either the individual day 4 measurement or of the change, reported as a ratio, between baseline and day 4. However, the functional strength of using the measurements from day 4 was limited in this instance because from this cohort of 107 patients there were only 60 values reported for day 4. To maximize the number of patients that were included in the analysis, a value for last (L) was obtained by taking the last value available for each patient from day 3 or later. It is noted that the AUC values for the last value were not significantly different than the values for the day 4 value from each biomarker, nor were the AUC values for the ratio of the 4:1 measurements or the L:F measurements. Consequently, for the remainder of this analysis the values used were the first (1), last (L) and the last to first (L:F) ratio.

TABLE 13

Individual AUC values from ROC analysis for mortality within 90 days

| | AUC Death 90 |
|---|---|
| BNP 1 | 0.602 |
| BNP 4 | 0.739 |
| BNP L | 0.729 |
| BNP R 4:1 | 0.684 |
| BNP R L:F | 0.684 |
| NTproBNP 1 | 0.735 |
| NTproBNP 4 | 0.836 |
| NTproBNP L | 0.824 |
| NTproBNP R 4:1 | 0.820 |
| NTproBNP R L:F | 0.776 |

TABLE 13-continued

Individual AUC values from ROC analysis for mortality within 90 days

| | AUC Death 90 |
|---|---|
| ST2 1 | 0.530 |
| ST2 4 | 0.889 |
| ST2 L | 0.773 |
| ST2 R 4:1 | 0.816 |
| ST2 R L:F | 0.838 |
| BUN | 0.830 |

Figure 17:
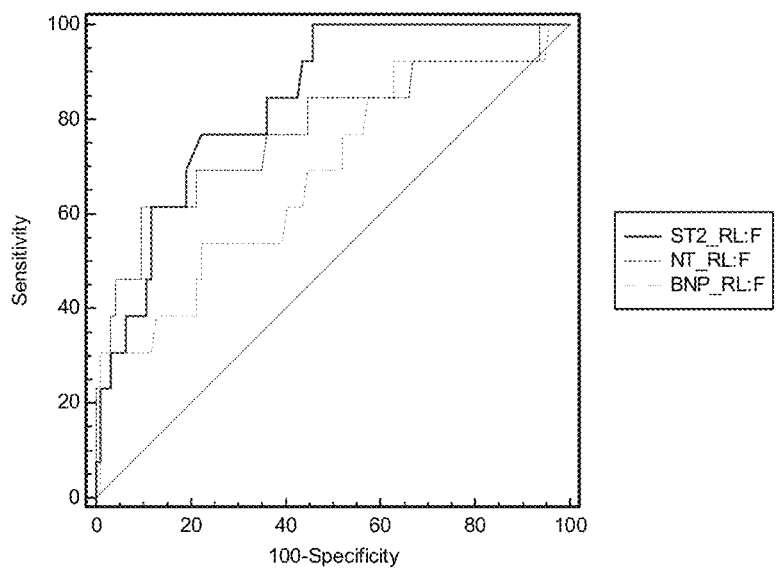
FIG. 17 is a line graph showing the results of ROC analysis of ratio values for mortality within 90 days.

FIG. 17 and Table 14 summarizes the ROC analysis for the L:F ratio values for each biomarker. In pairwise comparison none of the curves achieves statistically significant resolution.

TABLE 14

ROC analysis results of ratios for mortality within 90 days

| | AUC | SE | 95% CI |
|---|---|---|---|
| ST2_RL_F | 0.838 | 0.0708 | 0.754 to 0.902 |
| NT_RL_F | 0.776 | 0.079 | 0.685 to 0.851 |
| BNP_RL_F | 0.684 | 0.0859 | 0.587 to 0.770 |

Figure 18:
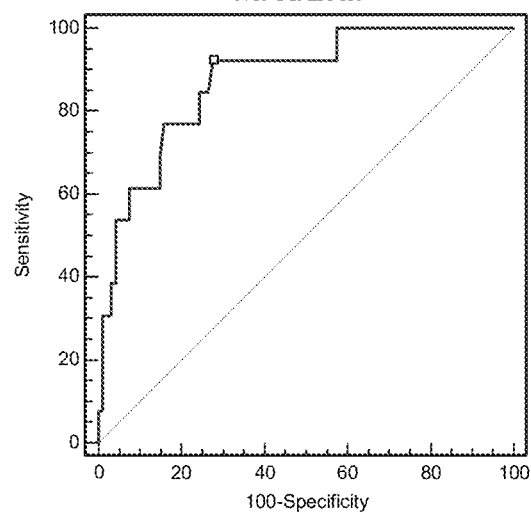
FIG. 18 is a line graph showing MACE risk formula ROC for mortality within 90 days.

As was determined using the peptide cohort data for derivation, the mortality risk score formula result yielded a ROC analysis AUC greater than any of the individual measurements or the ratio values. The ROC analysis for this formula is shown in FIG. 18 and the ROC analysis data summarized in Table 15.

TABLE 15

MACE risk score formula ROC data for mortality within 90 days

| Positive group | |
|---|---|
| Death90 | =1 |
| Sample size | 13 |
| Negative group | |
| Death90 | =0 |
| Sample size | 94 |
| Area under the ROC curve (AUC) | 0.876 |
| Standard error | 0.0639 |
| 95% Confidence interval | 0.798 to 0.931 |
| Significance level P (Area = 0.5) | 0.0001 |

Criterion values and coordinates of the ROC curve

| Criterion | Sensitivity | 95% CI | Specificity | 95% CI | +LR | −LR |
|---|---|---|---|---|---|---|
| >=1.67 | 100.00 | 75.1-100.0 | 0.00 | 0.0-3.9 | 1.00 | |
| >3.1 | 100.00 | 75.1-100.0 | 42.55 | 32.4-53.2 | 1.74 | 0.00 |
| >3.12 | 92.31 | 63.9-98.7 | 42.55 | 32.4-53.2 | 1.61 | 0.18 |
| >3.52* | 92.31 | 63.9-98.7 | 72.34 | 62.2-81.1 | 3.34 | 0.11 |
| >3.59 | 84.62 | 54.5-97.6 | 73.40 | 63.3-82.0 | 3.18 | 0.21 |
| >3.61 | 84.62 | 54.5-97.6 | 75.53 | 65.6-83.8 | 3.46 | 0.20 |
| >3.62 | 76.92 | 46.2-94.7 | 75.53 | 65.6-83.8 | 3.14 | 0.31 |
| >3.75 | 76.92 | 46.2-94.7 | 84.04 | 75.0-90.8 | 4.82 | 0.27 |

Figure 19:
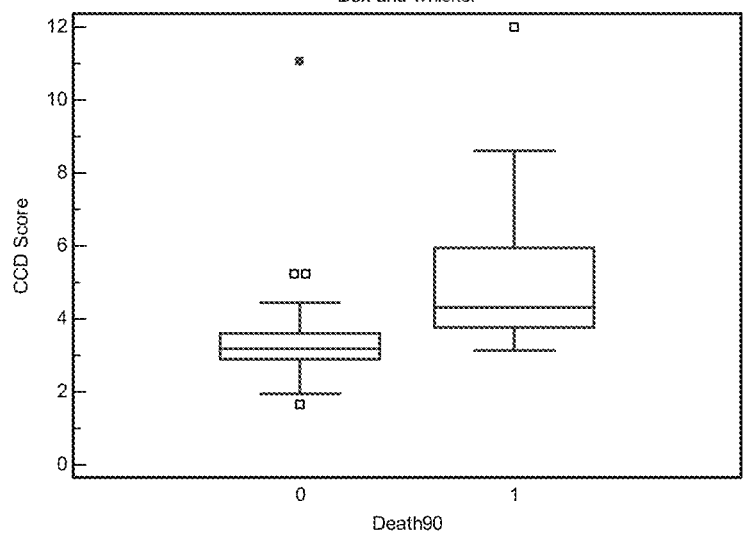
FIG. 19 is a whisker box plot showing MACE risk formula score for mortality within 90 days.
Figure 20:
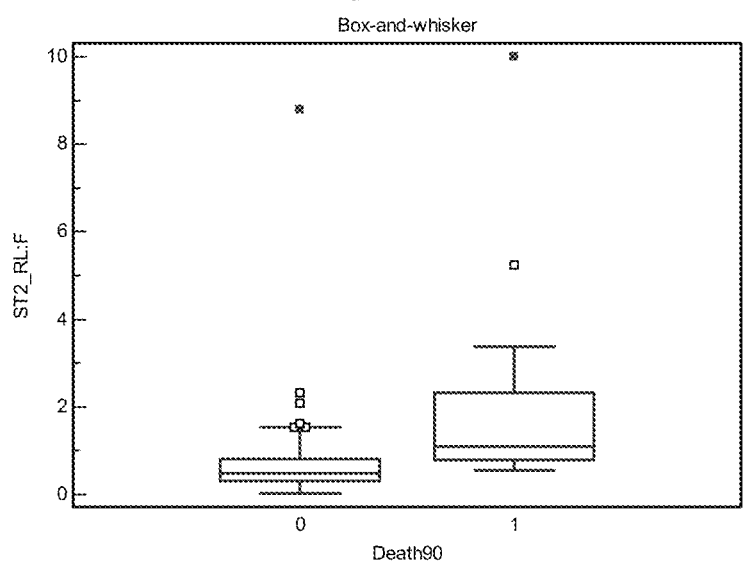
FIG. 20 is a whisker box plot showing ST2 R L:F for mortality within 90 days.

The ROC optimal value from this analysis was 3.52. As was noted using the peptide cohort data (see Example 1), the MACE risk score formula ROC optimal was also 3.5 but the best prognostic (mortality) accuracy was achieved with a value of 3.2 in that cohort. A basic whisker box plot (FIG. 19) shows clear resolution between the survivor and decedent groups, p<0.0001. For comparison, a whisker box plot analysis of the ST2 R L:F is similar, with a p=0.0001 (FIG. 20). As was also noted using the peptide cohort data a basic matrix analysis and relative risk calculation confirms that the MACE risk score provides the most accurate mortality prediction.

TABLE 16

Matrix and relative risk analysis of the strongest mortality prediction variables

|  | ST2 R L:F | | NTproBNP R L:F | | MACE risk score | |
| --- | --- | --- | --- | --- | --- | --- |
|  | <0.85 | ≥0.85 | <0.7 | ≥0.7 | <3.5 | ≥3.5 |
| N | 76 | 31 | 49 | 58 | 65 | 42 |
| N mortality | 3 | 10 | 2 | 11 | 1 | 12 |
| % mortality | 3.9% | 32.3% | 4.1% | 19.0% | 1.5% | 28.6% |
| PPV |  | 32.3% |  | 19.0% |  | 28.6% |
| NPV | 96.1% |  | 95.9% |  | 98.5% |  |
| RR |  | 8.2 |  | 4.6 |  | 18.6 |

Although both the ST2 ratio and the NTproBNP ratio yielded good relative risk values, the relative risk using the MACE risk score was much higher.

Conclusion

As was determined using the peptide cohort data (Example 1) the MACE risk score formula described herein provides the greatest prognostic accuracy, specifically when the outcome parameter is mortality, as determined by ROC, hazard ratio and relative risk calculation. There is a small but likely significant difference between the threshold values in these two cohorts. The peptide cohort described in Example 1 is an outpatient group with an ST2 ratio threshold of 0.75 and a MACE risk score formula threshold of 3.2, whereas the VET cohort described in this Example 2 is an inpatient group, and the respective threshold values are 0.85 and 3.5. This difference in threshold values may be due to the difference in disease severity between inpatient and outpatient conditions or may be due to the difference in time between measurements, as there was a 2 week time frame between measurements in the outpatient cohort as compared to a 3-5 day time frame in the inpatient cohort. Shimpo et al., Circulation 109(18):2186-90 (2004), reported that ST2 values increase rapidly for the first 12 hours following a myocardial infarction. The results described in these two examples clearly illustrate that there is also a dynamic change in ST2 levels in patients with heart failure but the absolute kinetic parameters are yet to be determined.

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method of treating a subject, the method comprising:
   (a) determining a first level of soluble ST2 in a biological sample comprising serum, blood, or plasma that is obtained from a subject at a first time point (ST2 T0) using an immunoassay comprising a monoclonal antibody that binds specifically to soluble ST2;
   (b) determining a second level of soluble ST2 in a biological sample comprising serum, blood, or plasma that is obtained from the subject at a second time point (ST2 T2) using the immunoassay comprising the monoclonal antibody that binds specifically to soluble ST2;
   (c) determining a level of a natriuretic peptide (NP) in a biological sample comprising serum, blood, or plasma that is obtained from the subject at the second time point (NP T1) using a monoclonal antibody that specifically binds to NP;
   (d) determining a MACE risk score (MACERS) for a subject using the following formula:

$$MACERS = (ST2\ T1/ST2\ T0) + \alpha\ \ln(NP\ T1),$$

wherein the coefficient $\alpha$ is a weighting factor for the variable it acts on;
   (e) identifying a subject having an elevated MACERS as compared to a reference MACERS; and
   (f) hospitalizing the subject identified in step (e).

2. The method of claim 1, wherein the coefficient $\alpha$ is about 0.33.

3. The method of claim 1, wherein the first time point is within 1 to 7 days of the onset of symptoms in the subject.

4. The method of claim 1, wherein the second time point is 2 to 14 days after the first time point.

5. The method of claim 1, wherein the reference MACERS is about 3.2.

6. The method of claim 1, wherein the subject has a body mass index (BMI) of 25-29, a BMI of ≥30, or impaired renal function.

7. The method of claim 1, wherein the subject is undiagnosed.

8. The method of claim 1, wherein the subject exhibits one or more non-specific symptoms.

9. A method of treating an undiagnosed subject, the method comprising:
   (a) determining a first level of soluble ST2 in a biological sample comprising serum, blood, or plasma that is obtained from an undiagnosed subject at a first time point (ST2 T0) using an immunoassay comprising a monoclonal antibody that binds specifically to soluble ST2;
   (b) determining a second level of soluble ST2 in a biological sample comprising serum, blood, or plasma that is obtained from the subject at a second time point (ST2 T2) using the immunoassay comprising the monoclonal antibody that binds specifically to soluble ST2;
   (c) determining a level of a natriuretic peptide (NP) in a biological sample comprising serum, blood, or plasma that is obtained from the subject at the second time point (NP T1) using a monoclonal antibody that specifically binds to NP;
   (d) determining a MACE risk score (MACERS) for the subject using the following formula:

$$MACERS = (ST2\ T1/ST2\ T0) + \alpha\ \ln(NP\ T1),$$

wherein the coefficient $\alpha$ is a weighting factor for the variable it acts on;
   (e) identifying a subject having an elevated MACERS as compared to a reference MACERS; and
   (f) treating the subject identified in step (e) with cardiac catheterization.

10. The method of claim 9, wherein the coefficient $\alpha$ is about 0.33.

11. The method of claim 9, wherein the first time point is within 1 to 7 days of the onset of symptoms in the subject.

12. The method of claim 9, wherein the second time point is 2 to 14 days after the first time point.

13. The method of claim 9, wherein the reference MAC-ERS is about 3.2.

14. The method of claim 9, wherein the subject has a body mass index (BMI) of 25-29, a BMI of ≥30, or impaired renal function.

15. The method of claim 9, wherein the subject exhibits one or more non-specific symptoms.

16. The method of claim 9, wherein the immunoassay comprising the monoclonal antibody that binds specifically to soluble ST2 is an enzyme-linked immunosorbent assay.

* * * * *

UNITED STATES PATENT AND TRADEMARK OFFICE
CERTIFICATE OF CORRECTION

PATENT NO. : 11,170,896 B2
APPLICATION NO. : 15/951376
DATED : November 9, 2021
INVENTOR(S) : James V. Snider and Eugene R. Heyman Page 1 of 1

It is certified that error appears in the above-identified patent and that said Letters Patent is hereby corrected as shown below:

In the Claims

Column 20, Line 13, in Claim 1, delete "α ln" and insert -- αln --, therefor.

Column 20, Line 57, in Claim 9, delete "α ln" and insert -- αln --, therefor.

Signed and Sealed this
Fifteenth Day of March, 2022

Drew Hirshfeld
*Performing the Functions and Duties of the
Under Secretary of Commerce for Intellectual Property and
Director of the United States Patent and Trademark Office*